United States Patent
Noguchi et al.

(10) Patent No.: US 11,642,056 B2
(45) Date of Patent: May 9, 2023

(54) PACKAGING CONTAINER, BLOOD TEST KIT, AND BLOOD ANALYSIS METHOD

(71) Applicant: FUJIFILM Corporation, Tokyo (JP)

(72) Inventors: Osamu Noguchi, Kanagawa (JP); Yasuko Hamamoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 367 days.

(21) Appl. No.: 16/391,337

(22) Filed: Apr. 23, 2019

(65) Prior Publication Data
US 2019/0350508 A1  Nov. 21, 2019

(30) Foreign Application Priority Data
May 15, 2018  (JP) .............................. JP2018-093815

(51) Int. Cl.
*A61B 5/15* (2006.01)
*G01N 33/49* (2006.01)
*B01L 3/00* (2006.01)

(52) U.S. Cl.
CPC .. *A61B 5/150351* (2013.01); *A61B 5/150343* (2013.01); *A61B 5/150755* (2013.01);
(Continued)

(58) Field of Classification Search
CPC ........ A61B 5/150351; A61B 5/150305; A61B 5/150343; A61B 5/150755; B01L 3/50; G01N 33/491
See application file for complete search history.

(56) References Cited

U.S. PATENT DOCUMENTS

| 5,415,282 A * | 5/1995 | Kienholz ................. A01N 1/02 206/216 |
| 10,101,318 B2 | 10/2018 | Nishijima et al. |

(Continued)

FOREIGN PATENT DOCUMENTS

| JP | 2000206111 | 7/2000 |
| JP | 2003270239 | 9/2003 |

(Continued)

OTHER PUBLICATIONS

YouTube. (2017). Video 1 Collecting, packaging and shipping samples. YouTube. https://www.youtube.com/watch?v=YdzKSal-NB0. (Year: 2017).*

(Continued)

*Primary Examiner* — Matthew D Krcha
*Assistant Examiner* — Tingchen Shi
(74) *Attorney, Agent, or Firm* — JCIPRNET

(57) ABSTRACT

Provided is a packaging container including a bag main body portion having a first surface, a second surface and an opening portion; and a tongue piece portion formed to be continuously extended from the first surface. The bag main body portion and the tongue piece portion have an aluminum vapor-deposited layer on an outside thereof, the packaging container further includes an adhesion portion which is provided on the second surface to be spaced from the opening portion; and a folded-back portion which is provided between the adhesion portion and the opening portion to fold back the tongue piece portion to the opening portion side. A length of the tongue piece portion is a, a length from the opening portion to the folded-back portion is b, and a length from the folded-back portion to the adhesion portion is c. And, $a < b + c.$

12 Claims, 15 Drawing Sheets

(52) U.S. Cl.
CPC ........... *A61B 5/150305* (2013.01); *B01L 3/50* (2013.01); *G01N 33/491* (2013.01)

(56) References Cited

U.S. PATENT DOCUMENTS

| | | | |
|---|---|---|---|
| 10,697,870 B2 | 6/2020 | Urano et al. | |
| 10,746,723 B2 | 8/2020 | Yamashita et al. | |
| 2002/0127419 A1* | 9/2002 | Kobayashi | B32B 15/20 428/513 |
| 2003/0065300 A1* | 4/2003 | Suga | A61F 15/003 604/385.02 |
| 2003/0175167 A1 | 9/2003 | Takanori et al. | |
| 2007/0292053 A1* | 12/2007 | Lin | B65D 31/02 383/120 |
| 2011/0019944 A1* | 1/2011 | Sargin | B65D 31/10 383/120 |
| 2017/0105707 A1* | 4/2017 | Senior | G01N 33/521 |

FOREIGN PATENT DOCUMENTS

| | | | |
|---|---|---|---|
| JP | 2006204387 | | 8/2006 |
| JP | 2012148791 | | 8/2012 |
| JP | 2012148791 A | * | 8/2012 |
| JP | 2013036986 | | 2/2013 |
| JP | 2016142564 | | 8/2016 |
| JP | 2016156756 | | 9/2016 |
| JP | 2016185820 | | 10/2016 |
| JP | 2017015710 | | 1/2017 |
| JP | 2017015713 | | 1/2017 |

OTHER PUBLICATIONS

"Office Action of Japan Counterpart Application", dated Jun. 25, 2021, with English translation thereof, p. 1-p. 6.

\* cited by examiner

FIG. 15

| CLOSURE TORQUE FOR CAP (N·m) | EVAPORATION RATE WITH NO PACKAGING CONTAINER (AFTER 7 DAYS) | EVAPORATION RATE WITH PACKAGING CONTAINER (AFTER 7 DAYS) |
|---|---|---|
| 4 | 6.4% | 3.3% |
| 6 | 5.2% | 3.3% |
| 8 | 3.3% | 2.4% |

PACKAGING CONTAINER, BLOOD TEST KIT, AND BLOOD ANALYSIS METHOD

CROSS-REFERENCE TO RELATED APPLICATIONS

The present application claims priority under 35 U.S.C. § 119 to Japanese Patent Application No. 2018-093815, filed on May 15, 2018. The above application is hereby expressly incorporated by reference, in its entirety, into the present application.

BACKGROUND OF THE INVENTION

1. Field of the Invention

The present invention relates to a packaging container, a blood test kit, and a blood analysis method, and particularly relates to a packaging container into which a blood specimen self-collected by a test subject is packaged, a blood test kit, and a blood analysis method.

2. Description of the Related Art

In general, blood collection includes general blood collection in which a certain qualified person such as a doctor collects blood from a vein using a syringe, and self-blood collection in which a test subject collects blood by piercing his finger or the like using a blood collecting needle. The blood collected by the self-blood collection is mailed to a medical institution or a test institution in a sealed state in a blood collection container, and tests are conducted therein. In a case where the blood is mailed without separating blood cells and plasma, a test is conducted after separating the blood into blood cells and plasma by a centrifuge at a medical institution or a test institute.

As a container into which a collection container is packaged, for example, JP2000-206111A discloses a packaging container for a vacuum blood collection tube, in which a zip portion is provided on the vicinity of an opening portion of a packaging container made of a multilayer film, and by heat sealing outside the zip portion, transpiration of an internal aqueous solution is prevented.

SUMMARY OF THE INVENTION

The blood collected by the self-blood collection is sealed in a blood collection tube, and a packaging container into which the blood collection tube is packaged, and is mailed to a medical institution or a test institution in a sealed state so as to be tested. In this case, in a case where the blood collection tube and the packaging container are not sufficiently sealed, a liquid in the blood collection tube evaporates at the time of mailing, and therefore a test with high accuracy could not be carried out. In addition, packaging a bottle and cap of the blood collection tube using a tape may be considered in order to improve sealability; however, an operation for extracting the blood becomes complicated.

JP2000-206111A mentioned above discloses that the packaging container is tightly sealed by the zip portion and heat sealing. However, a device is necessary in order to perform the heat sealing, and certainly zipping depends on a user. Therefore, it was hard to say that sealability is reliably maintained. In addition, because a heat sealed portion is cut out to open the zip, it was not easy to take out a blood collection tube.

The present invention has been made in view of the above circumstances, and an object thereof is to provide a packaging container by which sealability of the packaging container into which a liquid specimen collection tube is packaged is made to be compatible with easiness of extraction of a liquid from the liquid specimen collection tube. Another object thereof is to provide a blood test kit having the packaging container, and a blood analysis method using the blood test kit.

In order to achieve the object of the present invention, a packaging container according to the present invention is a packaging container into which a liquid specimen collection tube is packaged, the packaging container comprising: a bag main body portion; and a tongue piece portion, in which the bag main body portion is a packaging bag including a first surface and a second surface which define an inner space and having an opening portion provided on one end, the tongue piece portion is formed to be continuously extended from the opening portion side of the first surface, and the bag main body portion and the tongue piece portion include an aluminum vapor-deposited layer on an outside thereof, the packaging container further comprises: an adhesion portion that is provided on the second surface to be spaced from the opening portion; and a folded-back portion that is provided between the adhesion portion and the opening portion to fold back the tongue piece portion to the opening portion side, and the following relational expression is satisfied in a case where a length of the tongue piece portion is a, a length from the opening portion to the folded-back portion is b, and a length from the folded-back portion to the adhesion portion is c.

$$a < b + c$$

According to the present invention, by designing the length of each portion of the packaging container so that the above expression is satisfied, in a case where a user (a person who is a test subject) inserts a liquid specimen collection tube into the packaging container, folds back the packaging container, and makes adhesion at the adhesion portion so as to seal the packaging container, and in a case where the packaging container is folded back at the opening portion, that is, a case where the packaging container is folded back only at the tongue piece portion, the folded-back tongue piece portion does not reach the adhesion portion. In order to allow the folded-back bag main body portion or tongue piece portion to adhere to the adhesion portion, it is necessary to fold back the bag main body portion. By folding back at the bag main body portion, the opening portion can be reliably sealed. In addition, because the liquid specimen collection tube can be sealed in the packaging container, it is possible to prevent evaporation of a liquid by sealing the liquid specimen collection tube with a cap, and to easily extract a liquid specimen from the liquid specimen collection tube.

In one aspect of the present invention, it is preferable that the adhesion portion be provided to have a width in an opening direction of the packaging container, and the following relational expression be satisfied in a case where the width of the adhesion portion is d.

$$c < b < c + d$$

$$a + b > c + d$$

According to this aspect, firstly, by satisfying the expression of $c < b < c + d$, the opening portion can be pasted to the adhesion portion in a case of folding back the bag main body portion at the folded-back portion. Accordingly, it is possible to reliably seal the opening portion with the adhesion portion, thereby making it possible to reliably seal the inside of the packaging container. In addition, by satisfying the expression of a+b>c+d, a distal end of the tongue piece portion can be disposed beyond the adhesion portion in a case where the bag main body portion is folded back. Accordingly, because the distal end of the tongue piece portion is not pasted to the adhesion portion, it is possible to easily open the packaging container by holding the distal end of the tongue piece portion.

In one aspect of the present invention, it is preferable that an arrival position indicative of a position of the distal end of the tongue piece portion is indicated on the second surface of the bag main body portion in a case where the bag main body portion is folded back at the folded-back portion.

According to this aspect, by indicating the arrival position indicative of the position of the distal end of the tongue piece portion, a user adjusts the distal end of the tongue piece portion to this arrival position, thereby making it possible to adjust positions of the opening portion and the adhesion portion to a predetermined position. In a case where the distal end of the tongue piece portion is adjusted to the arrival position, by designing such that the opening portion is pasted to the adhesion portion, the opening portion can be sealed with the adhesion portion.

In one aspect of the present invention, it is preferable that an operation procedure for sealing the packaging container is indicated on the bag main body portion, and the operation procedure be a procedure in which the bag main body portion is folded back and the opening portion is pasted to a position of the adhesion portion.

According to this aspect, by indicating the operation procedure on the bag main body portion, it is possible to call attention of packaging procedures to a test subject who does not read an instruction manual.

In one aspect of the present invention, it is preferable that the folded-back portion have a crease.

According to this aspect, since the folded-back portion has a crease, a test subject can reliably fold back the bag main body portion at the folded-back portion in a case of performing packaging into the packaging container. Accordingly, by designing such that the opening portion is pasted to the position of the adhesion portion in a case where the bag main body portion is folded back at the folded-back portion, the opening portion can be sealed with the adhesion portion.

In one aspect of the present invention, it is preferable that a folded-back position be indicated at a position of the first surface, which corresponds to the folded-back portion of the bag main body portion.

According to this aspect, by indicating the folded-back position on the first surface, it is possible to perform packaging while checking at the folded-back position indicated on the first surface even after the bag main body portion is folded back at the folded-back portion.

It is preferable that one aspect of the present invention further comprise an adhesion portion on the first surface side of the tongue piece portion.

According to this aspect, by providing the adhesion portion on the first surface side of the tongue piece portion, after pasting the bag main body portion to the adhesion portion provided on the second surface, the bag main body portion is folded back to be pasted to the adhesion portion on the first surface side, and therefore the inside of the packaging container can be reliably sealed.

In one aspect of the present invention, it is preferable that a length from an end portion on a side opposite to the opening portion on the second surface of the bag main body portion to the adhesion portion be longer than a length in a longitudinal direction of the liquid specimen collection tube.

According to this aspect, in a case where the liquid specimen collection tube is inserted to the end portion on the side opposite to the opening portion of the packaging container, the adhesion portion and the liquid specimen collection tube do not overlap each other, and therefore the bag main body portion or tongue piece portion can be pasted to the adhesion portion in a plane state, thereby making it possible to paste them without a gap therebetween.

In one aspect of the present invention, it is preferable that a notch portion be formed on a side portion of the bag main body portion, and at a position on a side opposite to the opening portion with the adhesion portion interposed therebetween.

According to this aspect, by providing the notch portion and opening the packaging container from the notch portion, it is possible to easily take out the liquid specimen collection tube from the packaging container.

In one aspect of the present invention, it is preferable that the packaging bag be a gusset bag.

According to this aspect, by making the packaging bag into a gusset bag, it is possible to allow the packaging container to have a certain thickness. Accordingly, even in a state in which the liquid specimen collection tube is put into the packaging container, the bag main body portion or tongue piece portion can be pasted to the adhesion portion in a plane state, thereby making it possible to paste them without a gap therebetween.

In order to achieve the object of the present invention, a blood test kit according to the present invention comprises a blood collection instrument for collecting a blood specimen; a dilute solution for diluting the collected blood specimen; a liquid specimen collection tube including separation means for recovering a plasma component from the diluted blood specimen; and the packaging container described above. A concentration of a target component in the blood specimen is analyzed using a standard component constantly present in blood or a standard component not present in blood but contained in the dilute solution.

According to the blood test kit of the present invention, by using the above-described packaging container, it is possible to inhibit evaporation of blood in the liquid specimen collection tube packaged thereinto, and therefore analysis can be performed with high accuracy.

In order to achieve the object of the present invention, a blood analysis method according to the present invention is a blood analysis method which uses the blood test kit described above, the blood analysis method comprising: creating a correction table based on an evaporation rate of the blood specimen in the packaging container which is in a sealed state; setting a correction parameter of the blood specimen based on the correction table; and correcting a concentration of a target component in the blood specimen using the correction parameter.

According to the present invention, since the evaporation of blood can be inhibited by using the above-described packaging container, it is possible to lower a value of the evaporation rate of the blood specimen with respect to the sealed state of the packaging container, and to reduce a fluctuation in evaporation rate. Accordingly, by setting the correction parameter and correcting the concentration of the target component, analysis can be performed with higher accuracy.

In one aspect of the present invention, it is preferable that the correction table be created based further on at least one of the number of days from a collection date to an analysis date of the blood specimen, or a closure torque for a cap of the liquid specimen collection tube.

According to this aspect, an example of parameters for creating the correction table is shown. By using the above-mentioned parameter, it is possible to perform accurate correction in relation to an evaporation amount in the liquid specimen collection tube.

According to the packaging container of the present invention, the length of the tongue piece portion is made to be shorter than the length from the opening portion to the adhesion portion. Therefore, in order to paste the folded back tongue piece portion or bag main body portion to the adhesion portion, it is necessary to fold back the bag main body portion. Accordingly, by folding back the bag main body portion of the packaging container, it is possible to improve sealability of a space inside the bag main body portion. By improving sealability of the packaging container, evaporation of a liquid can be inhibited even in a case where sealability of the liquid specimen collection tube is weak. As described above, since the sealability of the liquid specimen collection tube needs not to be improved, it is not necessary to use a seal tape or the like, and therefore a liquid specimen can be easily extracted.

BRIEF DESCRIPTION OF THE DRAWINGS

FIG. 15 is a table showing a closure torque for a cap of a liquid specimen collection tube and an evaporation rate depending on whether or not the liquid specimen sampling tube is stored in the packaging container.

DESCRIPTION OF THE PREFERRED EMBODIMENTS

Hereinafter, a packaging container, a blood test kit, and a blood analysis method according to the present invention will be described with reference to the accompanying drawings. According to the present specification, a numerical value range indicated using "to" means a range including the numerical values described before and after "to" as a lower limit value and an upper limit value. A standard component constantly present in the blood may be referred to as an external standard substance or an external standard. In addition, a standard component not present in the blood may be referred to as an internal standard substance or an internal standard.

Blood Test Kit

Figure 1:
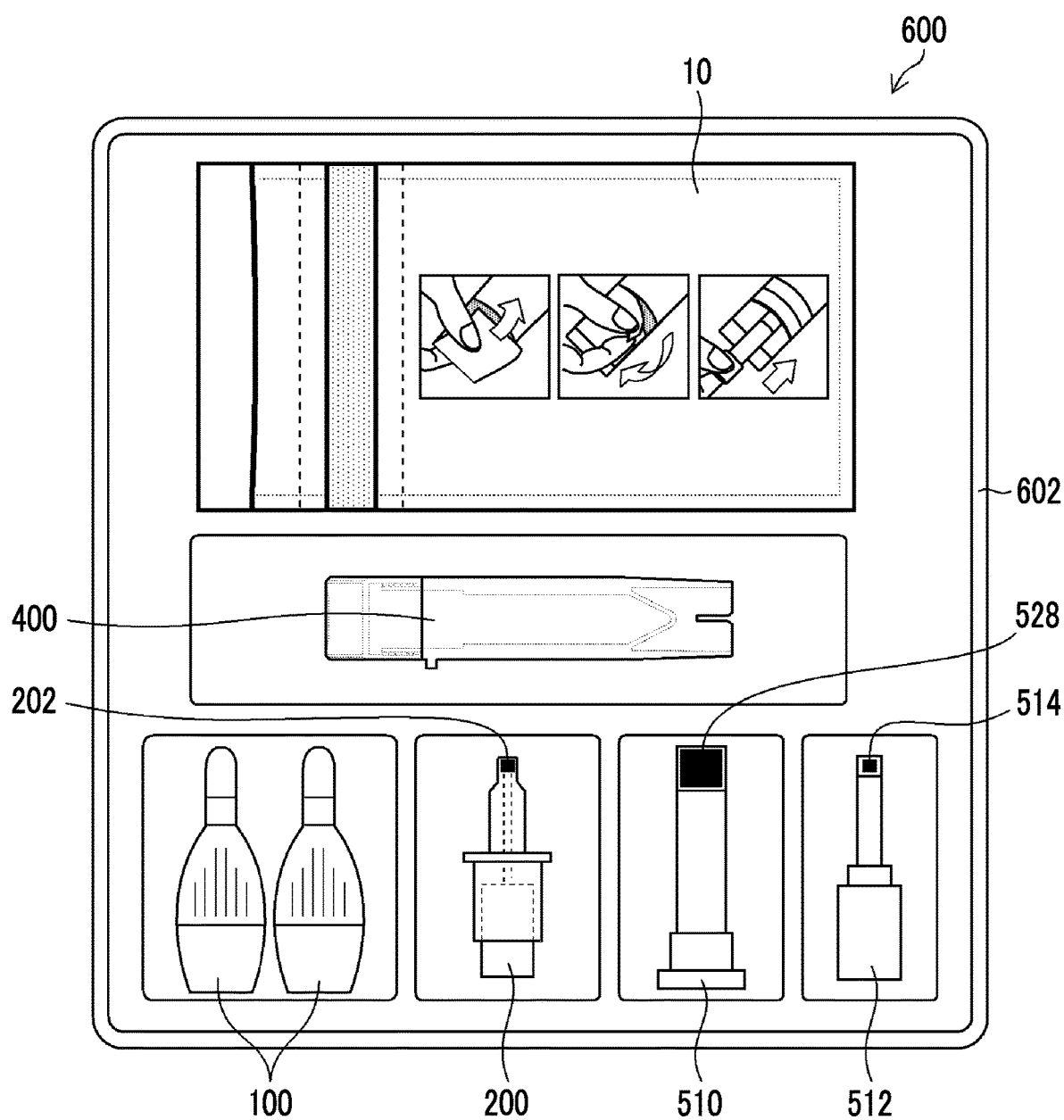
FIG. 1 is a configuration view showing an example of a blood test kit.

First, a blood test kit of the present invention will be described. FIG. 1 is a configuration view showing an example of a blood test kit. A blood test kit 600 shown in FIG. 1 comprises a cap 512 having a sealing member 514, a cylinder 510, a blood collection instrument 200, a lancet 100, and an accommodation instrument 400 containing a dilute solution. In addition, the blood test kit 600 comprises a packaging container 10 into which a liquid specimen collection tube containing collected blood is packaged for mailing. In the blood test kit 600 shown in FIG. 1, a tube in which the cylinder 510 is inserted into the accommodation instrument 400, and the accommodation instrument 400 is hermetically sealed with the cap 512 serves as a liquid specimen collection tube.

The cap 512, the cylinder 510, the blood collection instrument 200, the lancet 100, the accommodation instrument 400, and the packaging container 10 are housed in a case 602. The blood test kit 600 may comprise an adhesive plaster and a cloth for sterilization (not shown).

Hereinafter, a configuration of the blood test kit 600 will be described below.

Accommodation Instrument

Figure 2:
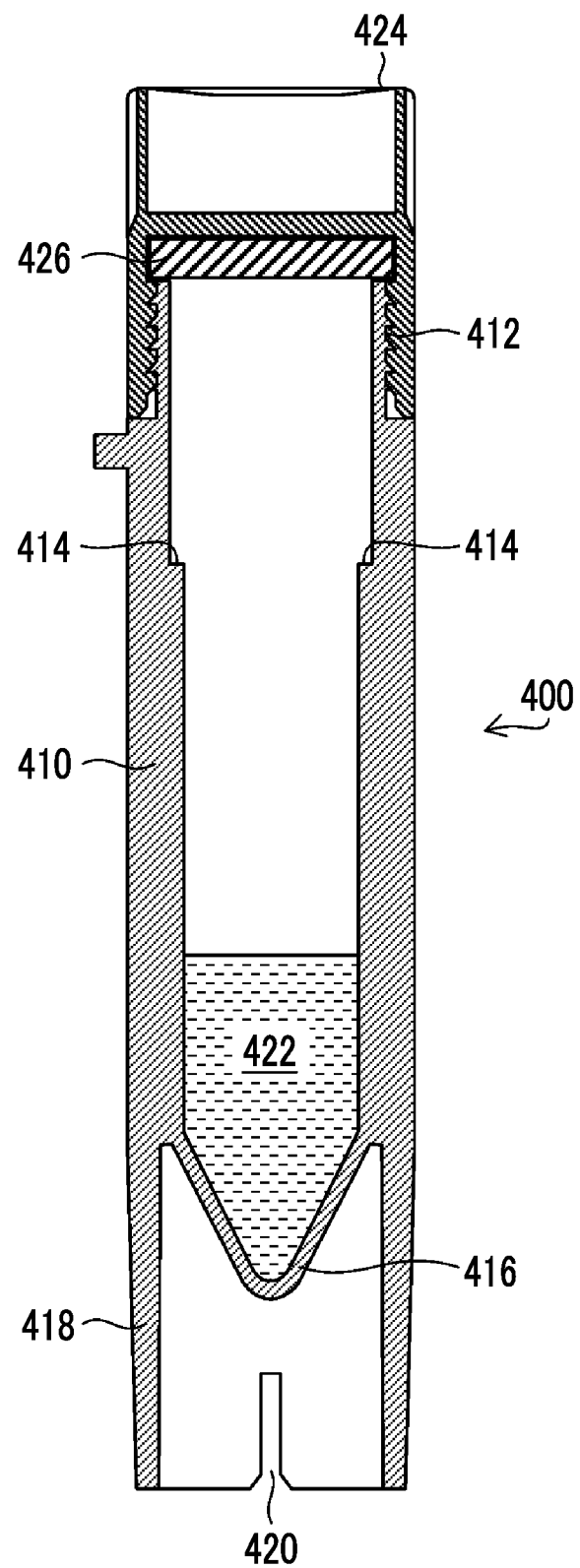
FIG. 2 is a view showing an example of a configuration of an accommodation instrument for accommodating a dilution of a blood specimen.

FIG. 2 is a cross-sectional view showing an example of a configuration of an accommodation instrument for accommodating a dilution of a blood specimen. As shown in FIG. 2, the accommodation instrument 400 has a cylindrical blood collection container 410 of a transparent material. On an upper end side of the blood collection container 410, a screw portion 412 is formed on the outer surface, and an engaging portion 414 is protruded on the inner surface. In addition, a conical bottom portion 416 protruding toward a lower end side is formed at a lower end portion of the blood collection container 410. A cylindrical leg portion 418 is formed around the bottom portion 416. The term "upper" and "lower" mean "upper" and "lower" in a state in which the leg portion 418 is placed on the placement surface.

The leg portion 418 has the same outer diameter as that of a sample cup (not shown) used when performing an analytical test of blood, and each of slit grooves 420 is formed in a vertical direction at positions facing, preferably a lower end thereof. In addition, as shown in FIG. 2, it is preferable that a required amount, for example, 500 mm$^3$ of a dilute solution 422 be accommodated in the blood collection container 410.

As shown in FIG. 2, it is preferable that an upper end opening of the blood collection container 410 be hermetically sealed with a cap 424 via a packing 426 before using the accommodation instrument 400.

Standard Component Constantly Present in Blood

For accurate analysis of a concentration present in plasma of the blood before dilution with respect to a target component after dilution of diluted plasma, in which a dilution factor of plasma components is high, it is possible to employ a method of obtaining from a rate of change in concentration of a substance preliminarily present in the dilute solution. In addition, it is also possible to employ a method for analyzing a concentration of a target component in a blood specimen using a standard component constantly present in the blood. In a case of analyzing blood components from a smaller amount of blood, a case of employing a method using a standard component constantly present in the blood is preferable, because it is possible to perform measurement with a small measurement error. Accordingly, as the blood test kit of the embodiment of the present invention, the blood test kit for analyzing a concentration of a target component in a blood specimen using a standard component constantly present in the blood is one of preferred embodiments.

Here, the term "using" a standard component means to determine a dilution factor for analyzing a concentration of a target component based on a standard value for a standard component (a constant value in a case of using the standard component constantly present in the blood). Accordingly, a case of analyzing a concentration of a target component in a blood specimen using a standard component constantly present in the blood, also means that a dilution factor is determined based on a constant value (standard value) of the standard component constantly present in the blood, and that a concentration of a target component is analyzed.

Examples of the standard component constantly present in the blood include sodium ion, chloride ion, potassium ion, magnesium ion, calcium ion, total protein, albumin, and the like. Concentrations of these standard components contained in serum and plasma of a blood specimen are as follows: a concentration of sodium ion is 134 mmol/L to 146 mmol/L (average value: 142 mmol/L), a concentration of chloride ion is 97 mmol/L to 107 mmol/L (average value: 102 mmol/L), a concentration of potassium ion is 3.2 mmol/L to 4.8 mmol/L (average value: 4.0 mmol/L), a concentration of magnesium ion is 0.75 mmol/L to 1.0 mmol/L (average value: 0.9 mmol/L), a concentration of calcium ion is 4.2 mmol/L to 5.1 mmol/L (average value: 4.65 mmol/L), a concentration of total protein is 6.7 g/100 ml to 8.3 g/100 ml (average value: 7.5 g/100 mL), a concentration of albumin is 4.1 g/100 mL to 5.1 g/100 mL (average value: 4.6 g/100 mL). The embodiment is for making it possible to measure a target component in a case where an amount of blood to be collected is extremely small to ease the pain of a subject, and therefore, in a case of diluting a small amount of blood in a dilute solution, it is necessary to accurately measure a concentration of the "standard component constantly present in the blood," which is present in the dilute solution. In a case where a dilution factor increases, a concentration of components originally present in the blood in the dilute solution decreases, and therefore, depending on a dilution factor, there is a possibility of including a measurement error when measuring a concentration. Therefore, in order to sufficiently and precisely detect the standard component in a case where a small amount of blood components is diluted by a high dilution factor, it is preferable to measure the standard component present in a small amount of blood at a high concentration. In the present invention, it is preferable to use sodium ion ($Na^+$) or chloride ion ($Cl^+$) present at a high concentration among components constantly present in the blood specimen. Furthermore, it is most preferable to measure sodium ions having the highest amount present in the blood among the above-mentioned standard components constantly present in the blood. For sodium ions, an average value represents a standard value (a median value within a reference range), and this value is 142 mmol/L and occupies 90 mol % or more of total cations in the plasma.

Standard Component not Present in Plasma

One of preferred aspects of the embodiment is a blood test kit for analyzing a concentration of a target component in a blood specimen using a standard component not present in the blood. Such a blood test kit may be a kit for using a standard component not present in the blood, together with a standard component constantly present in the blood, or may be a kit for using only a standard component not present in the blood without using a standard component constantly present in the blood.

In any case, the standard component not present in the blood can be used by being added to a dilute solution to be described later such that a concentration becomes a predetermined concentration. As a standard component not present in the blood, it is possible to use a substance which is not contained in the blood specimen at all or which is contained by an extremely small amount. As a standard component not present in the blood, it is preferable to use a substance that does not interfere with the measurement of a target component in the blood specimen, a substance that does not decompose under the action of a biological enzyme in the blood specimen, a substance that is stable during dilution, a substance that does not permeate the blood cell membrane, and thus is not contained in the blood cell, a substance that does not adsorb to a storage container of a buffer solution, and a substance for which a detection system performing measurement with high accuracy can be used.

A standard component not present in the blood is preferably a substance that is stable even in a state of being added to and stored in a dilute solution for a long period of time. Examples of standard components not present in the blood include glycerol triphosphate, Li, Rb, Cs, or Fr as alkali metals, and Sr, Ba, or Ra as alkaline earth metals, among which Li and glycerol triphosphate are preferred.

These standard components not present in the blood can be color-developed by adding a second reagent when measuring a concentration after blood dilution, and a concentration in the diluted blood can be obtained from a color density. For example, regarding the measurement of lithium ions added to the dilute solution, a large amount of sample can be easily measured with a small amount of sample with an automatic biochemistry analyzer by using a chelate colorimetric method (halogenated porphyrin chelating method: perfluoro-5,10,15,20-tetraphenyl-21H,23H-porphyrin).

Dilute Solution

The blood test kit contains a dilute solution to dilute the collected blood specimen. In a case where the blood test kit is for analyzing a concentration of a target component in the blood specimen using the standard component constantly present in the blood, the dilute solution does not contain a standard component constantly present in the blood. The phrase "not containing" means "substantially not containing." Here, the phrase "substantially not containing" means that any homeostatic substance to be used for obtaining a dilution factor is not used at all, or even in a case where the substance is contained, the substance is contained to the extent that a concentration of a small amount does not affect the measurement of a homeostatic substance in the dilute solution after diluting the blood specimen. In a case where sodium ions or chloride ions are used as a standard component constantly present in the blood, a dilute solution substantially not containing sodium ions or chloride ions is used as a dilute solution.

A pH of the blood is kept constant from a normal pH of 7.30 to a pH of about 7.40 in healthy subjects. Therefore, in order to prevent decomposition or denaturation of the target component, the dilute solution is preferably a buffer solution having a buffering action in a pH region within an range of pH 6.5 to pH 8.0, preferably within a range of pH 7.0 to pH 7.5, and more preferably within a range of pH 7.3 to pH 7.4;

and the dilute solution is preferably a buffer solution containing a buffer component that suppresses variations in pH.

In the related art, as the type of a buffer solution, an acetate buffer solution (Na), a phosphate buffer solution (Na), a citrate buffer solution (Na), a borate buffer solution (Na), a tartrate buffer solution (Na), a tris(hydroxymethyl) aminoethane (Tris) buffer solution (Cl), a [2-[4-(2-hydroxyethyl)-1-piperazinyl]ethanesulfonic acid] (Hepes) buffer solution, and a phosphate buffered saline (Na) are known. Among them, as a buffer solution in the vicinity of pH 7.0 to pH 8.0, a phosphate buffer solution, a Tris buffer solution, and a Hepes buffer solution are representative. However, there are conditions that, because a phosphate buffer solution contains a sodium salt of phosphoric acid and a Tris buffer solution has a dissociation pKa of 8.08, in order to impart buffering ability in the vicinity of pH 7.0 to pH 8.0, the buffer solution is generally used in combination with hydrochloric acid; and that a pKa of dissociation of sulfonic acid of Hepes is 7.55, but in order to adjust the buffer solution with constant ionic strength, a mixture of sodium hydroxide, sodium chloride, and HEPES is generally used. When seen from these conditions, these buffer solutions are useful as a buffer solution having an action of keeping a pH constant. However, these buffer solutions contain sodium ions or chloride ions which are substance preferably used as an external standard substance in the embodiment, and therefore application thereof is not preferable in a case where the blood test kit is for analyzing a concentration of a target component in the blood specimen using the standard component constantly present in the blood.

In a case where the blood test kit is for analyzing a concentration of a target component in the blood specimen using the standard component constantly present in the blood, a buffer solution to be used preferably does not contain sodium ions or chloride ions (where a meaning of the phrase, "does not contain" is as already described). Such a buffer solution preferably contains at least one amino alcohol compound selected from the group consisting of 2-amino-2-methyl-1-propanol (AMP), 2-ethylamino ethanol, N-methyl-D-glucamine, diethanolamine, and triethanolamine; and contains a dilute solution containing a buffering agent selected from the group consisting of 2-[4-(2-hydroxyethyl)-1-piperazinyl]ethanesulfonic acid (pKa=7.55), which is also referred to as HEPES that is a Good's buffer solution is a buffering agent having a pKa of around 7.4; N-tris(hydroxymethyl)methyl-2-aminoethanesulfonic acid (pKa=7.50) also called TES; 3-morpholinopropanesulfonic acid (pKa=7.20) also called MOPS; and N,N-bis(2-hydroxyethyl)-2-aminoethanesulfonic acid (pKa=7.15) also called BES. Among them, a combination of 2-amino-2-methyl-1-propanol (AMP) and HEPES, TES, MOPS, or BES is preferable, and furthermore, a combination of 2-amino-2-methyl-1-propanol (AMP) and HEPES is most preferable. pKa represents an acid dissociation constant.

In order to prepare the above buffer solution, it is sufficient that an amino alcohol and a Good's buffer solution is mixed at a concentration ratio of 1:2 to 2:1, preferably 1:1.5 to 1.5:1, and more preferably 1:1. A concentration of the buffer solution is not limited, but a concentration of the amino alcohol or Good's buffer solution is 0.1 mmol/L to 1000 mmol/L, preferably 1 mmol/L to 500 mmol/L, and more preferably 10 mmol/L to 100 mmol/L.

A chelating agent, a surfactant, an antibacterial agent, a preservative, a coenzyme, a saccharide, and the like may be contained in the buffer solution in order to keep an analysis target component stable. Examples of chelating agents include ethylenediamine tetraacetic acid (EDTA) salt, citric acid salt, oxalic acid salt, and the like. Examples of surfactants include a cationic surfactant, an anionic surfactant, an amphoteric surfactant, and a nonionic surfactant. Examples of preservatives include sodium azide, antibiotics, and the like. Examples of coenzymes include pyridoxal phosphate, magnesium, zinc, and the like. Examples of saccharides of an erythrocyte stabilizing agent include mannitol, dextrose, oligosaccharide, and the like. In particular, by adding antibiotics, it is possible to suppress the growth of bacteria partially mixed from a surface of the fingers at the time collecting blood from the fingers, to suppress decomposition of biological components due to bacteria, and to stabilize biological components.

The buffer solution also contains the standard component not present in the blood in the blood test kit for analyzing a target component using a standard component not present in the blood. It is also important not to contain an internal standard substance to be described later and not to interfere with a measurement system of blood analysis.

From the viewpoint of diluting the whole blood, it is possible to prevent hemolysis of blood cells by making an osmotic pressure of the buffer solution to be equal to or more than that of blood (285 mOsm/kg (where, mOsm/kg represents an osmotic pressure that 1 kg water of a solution has, and represents millimolar number of ions)). An osmotic pressure can be isotonically adjusted with salts, saccharides, buffering agents, or the like, which do not affect the measurement of a target component and the measurement of the standard component constantly present in the blood. An osmotic pressure of the buffer solution can be measured by an osmometer.

In a case of testing a specific organ or a specific disease such as liver function, renal function, metabolism, and the like as a blood test, analysis of a plurality of target components to be measured is generally performed at the same time in order to perform a prediction and the like of a state of the organ, a lifestyle habit, and the like by obtaining information of the plurality of target components to be measured which are specific to the organ or the disease. For example, in order to examine the condition of the liver, concentrations of several or more substances in the blood, such as alanine transaminase (ALT), aspartate aminotransferase (AST), γ glutamyl transpeptidase (γ-GTP), alkaline phosphatase (ALP), total bilirubin, total protein, and albumin, are generally measured. As above, in order to measure the plurality of target components from one blood specimen, a certain volume of diluted blood is required in a case of considering a possibility of measuring again. Accordingly, regarding a dilute solution for diluting the collected blood, it is important that a certain volume thereof is secured. However, in consideration of minimizing the invasiveness to a test subject, an amount of blood collected is small, and therefore a dilution factor is, for example, 7 times or more, which is a high rate.

Blood Collection Instrument

Figure 3:
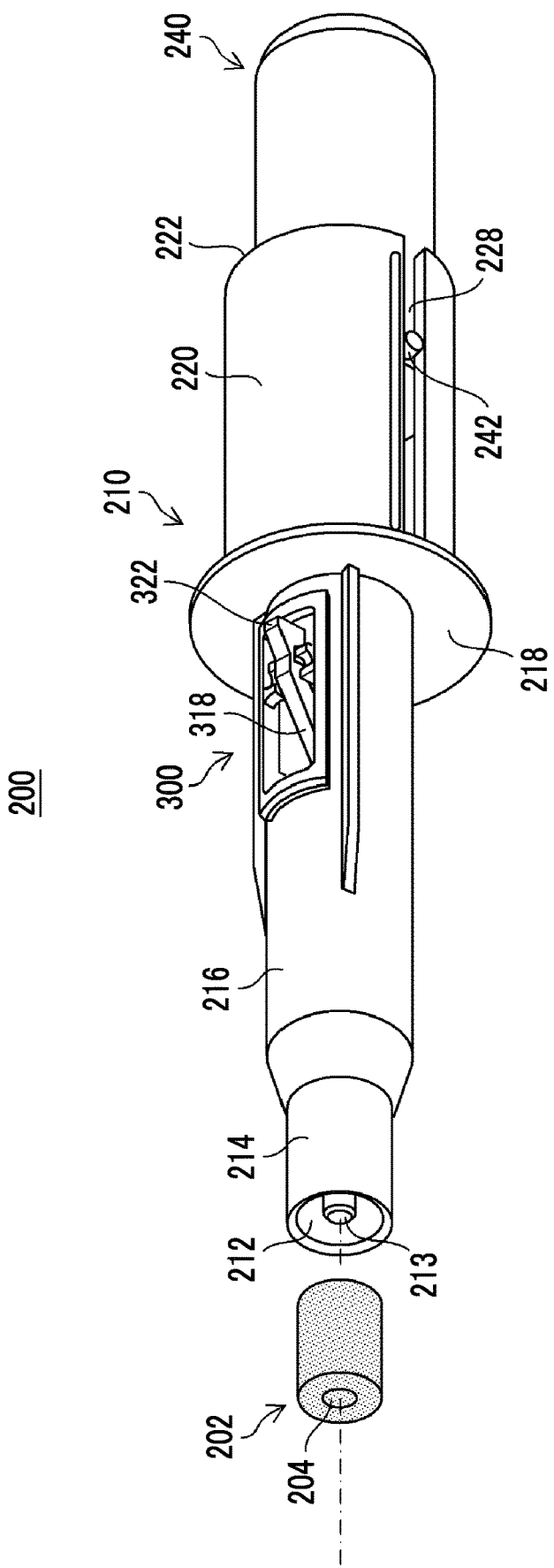
FIG. 3 is a view showing an example of a configuration of a blood collection instrument.

FIG. 3 is a perspective view of the blood collection instrument 200. As shown in FIG. 3, the blood collection instrument 200 comprises a case 210 in which an opening 212 is defined on one side, and a fiber rod 202 attachably and detachably held on the side of the opening 212. The case 210 comprises a distal end accommodation portion 214 for accommodating the fiber rod 202 on the other side from the side of the opening 212, a central portion 216, a flange portion 218, and a base end accommodation portion 220. The base end accommodation portion 220 has an opening 222, and an extrusion rod 240 is inserted from the opening 222. The case 210 is an integral molding, and the opening 212 and the opening 222 pass through therethrough.

The fiber rod 202 is attachably and detachably held in the distal end accommodation portion 214. The distal end accommodation portion 214 comprises a member 213 inserted into a space 204 of the fiber rod 202, whereby the fiber rod 202 is held. A central portion 216 has a locking lever 300. The extrusion rod 240 has an opening (not shown) to be engaged with a distal end of a lever 318 of the locking lever 300. By moving a lever operation portion 322 of the lever 318, the engagement between the distal end of the lever 318 and the opening is released. By moving the extrusion rod 240 in a longitudinal direction, the fiber rod 202 can be removed from the distal end accommodation portion 214.

The base end accommodation portion 220 has a slide groove 228 along an axial direction of the blood collection instrument 200. By inserting a protrusion 242 directed toward the extrusion rod 240 into the slide groove 228, the extrusion rod 240 rotating around the axial direction is restricted.

In collection of a blood specimen by the blood collection instrument 200, the fiber rod 202 held by the case 210 of the blood collection instrument 200 is brought into contact with a blood specimen which leaks outside the skin by damaging a fingertip or the like by a test subject himself or herself using a lancet for blood collection described above. Because the blood specimen is absorbed in a space of the fiber rod 202, the blood specimen can be collected in the fiber rod 202. At the time when it is confirmed that the fiber rod 202 becomes red in its entirety, collection of the blood specimen is completed.

Dilution of Blood Specimen

A cap 424 is removed from the blood collection container 410 of the accommodation instrument 400. The fiber rod 202 that has absorbed the blood specimen by the blood collection instrument 200 is introduced into a dilute solution 422 from an upper end opening of the blood collection container 410. The upper end opening of the blood collection container 410 is sealed with the cap 424.

Figure 4:
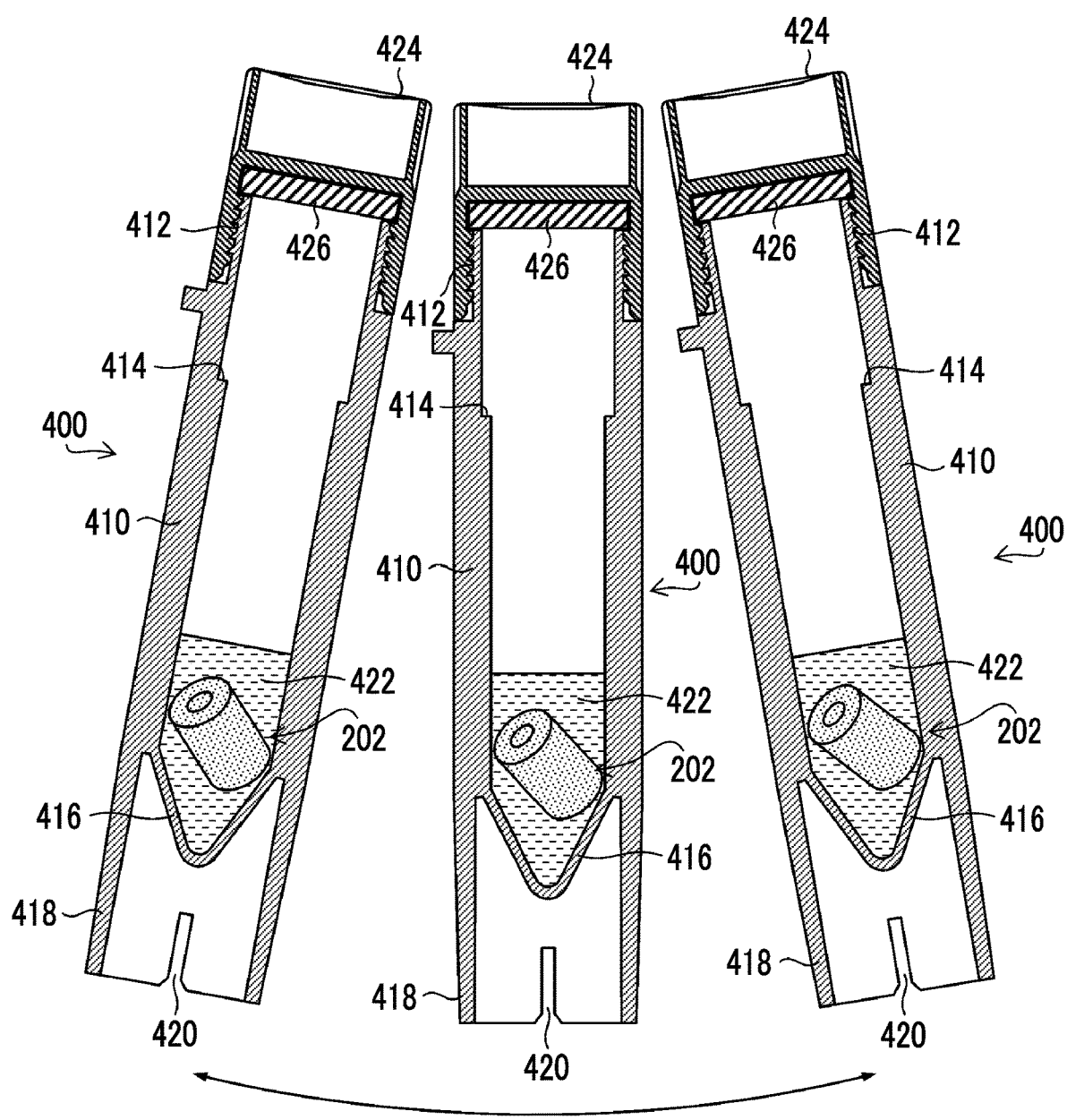
FIG. 4 is a view showing an example of releasing a blood specimen from a fiber rod.

As shown in FIG. 4, an upper portion of the blood collection container 410 is held, the blood collection container 410 is shaken several times in a pendulum shape, and the blood specimen is released from the fiber rod 202 to the dilute solution 422. By diluting the blood specimen into the dilute solution 422, a dilution of the blood specimen is accommodated in the accommodation instrument 400.

In a case where the dilute solution 422 turns red as a whole, shaking of the blood collection container 410 is ended.

Separation Instrument

The blood specimen collected by the blood collection instrument 200 may have been in a diluted state for a long time in the accommodation instrument 400 until analysis is performed thereon. Meanwhile, for example, in a case where hemolysis of erythrocytes occurs, there is a possibility that substances and enzymes and the like present in the blood cells elute into the plasma or serum, and thus test results are affected; or that the absorption of eluted hemoglobin affects a case of measuring an amount of analysis target component with light information such as optical absorption of the analysis target component. Therefore, it is preferable to prevent hemolysis. For this reason, the blood test kit contains a separation instrument for separating and recovering plasma components from a dilution of a blood specimen. A preferred example of the separation instrument is a separation membrane. The separation membrane can be used in the following manner. For example, the separation membrane captures blood cell components, allows plasma components to pass through, separates blood cells, and recovers the plasma components by applying pressure to a dilution of a blood specimen. In this case, it is preferable to use an anticoagulant. In addition, in order to ensure the measurement accuracy, it is preferable that the plasma which has passed through the separation membrane does not flow back to the blood cell side. In order to realize this, specifically, a backflow prevention means disclosed in JP2003-270239A can be used as a component of the kit.

Figure 5:
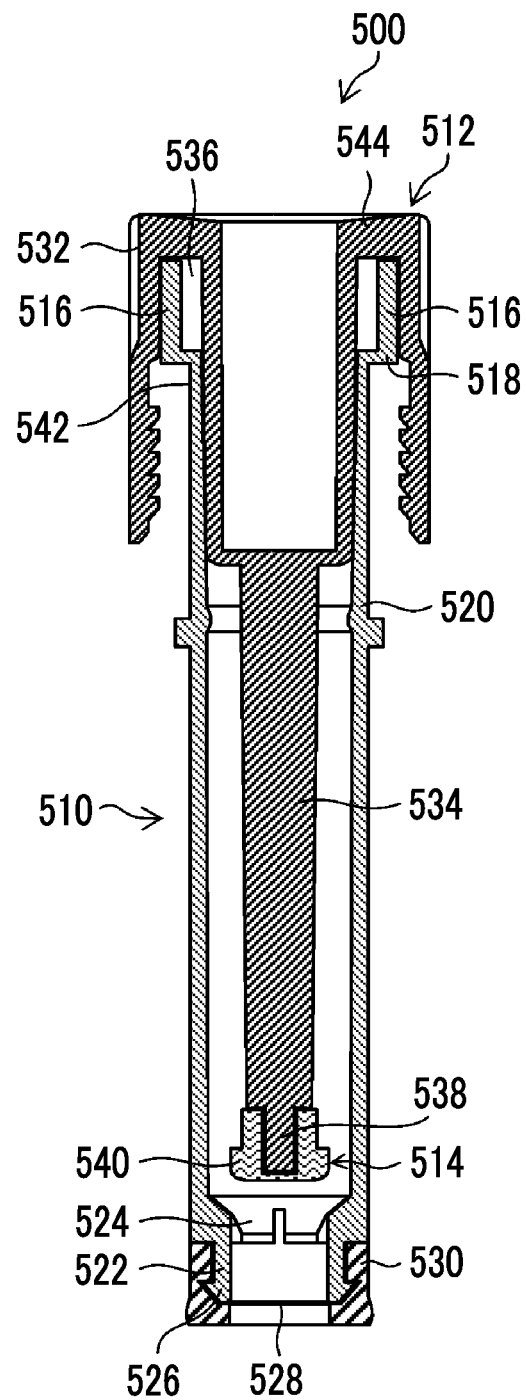
FIG. 5 is a view showing an example of a holding tool for holding a separation instrument.

FIG. 5 is a view showing an example of a holding tool having the separation instrument. A holding tool 500 shown in FIG. 5 is configured by combining the cap 512 shown in FIG. 1 and the cylinder 510. The cylinder 510 can be fitted into the blood collection container 410 of the accommodation instrument 400. The cap 512 can be screwed to the accommodation instrument 400, and a lower end of the cap 512 comprises a sealing member 514 for preventing the plasma in the cylinder 510 from flowing back into the blood collection container 410.

The cylinder 510 is made of a transparent material and has a cylindrical shape. A diameter expanding portion 516 is formed at an upper end portion 542 of the cylinder 510. The diameter expanding portion 516 is connected to a main body portion 520 via a thin-walled portion 518. A diameter reducing portion 522 is formed at a lower end portion of the cylinder 510. An engaging protrusion portion 524 is formed on an inner surface of the diameter reducing portion 522. Furthermore, an outer flange portion 526 is formed at a lower end portion of the diameter reducing portion 522. A lower end opening portion of the outer flange portion 526 is covered with a filtration membrane 528 functioning as a separation instrument. The filtration membrane 528 is configured to allow plasma in the blood to pass through and to block passage of blood cells. A cover 530 made of silicone rubber is mounted on an outer periphery of the diameter reducing portion 522.

The cap 512 is configured of a substantially cylindrical handle portion 532 and a mandrel portion 534 which is concentric with the handle portion 532 and extends downward. A cylindrical space 536 into which the diameter expanding portion 516 of the cylinder 510 can be fitted is formed at an inner upper end portion of the handle portion 532, and a lower side thereof is threaded and can be screwed into a screw. A lower end portion 538 of the mandrel portion 534 is formed in a pin shape, and a sealing member 514 is attachably and detachably provided on the lower end portion 538. The sealing member 514 is made of silicone rubber. A substantially cylindrical shape in which the lower end portion of the sealing member 514 is formed in an outer flange shape, and a level difference portion 540 is formed over the outer periphery. The handle portion 532 has a top portion 544, and an inner surface of the top portion 544 and the diameter expanding portion 516 are in contact with each other.

Figure 6:
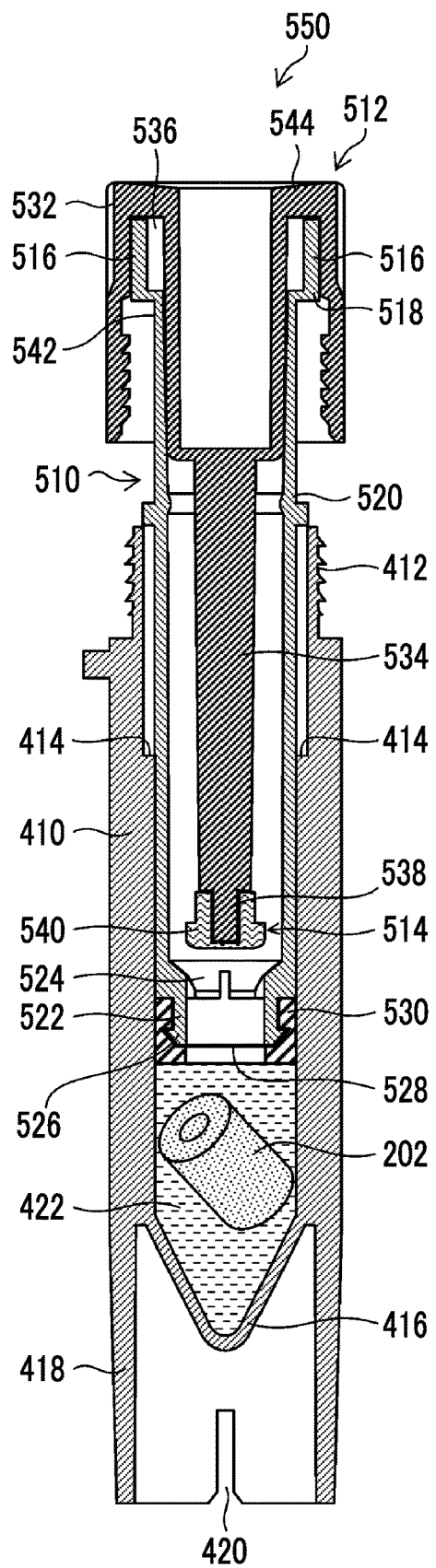
FIG. 6 is a view showing an example of a holding tool for holding a separation instrument.

Next, as shown in FIG. 6, a cap 424 and a packing 426 are removed from the blood collection container 410, from the blood collection container 410 in which the fiber rod 202 and a dilution of the blood specimen are contained. In this state, the cylinder 510 to which the cap 512 is attached is fitted into the blood collection container 410.

Figure 7:
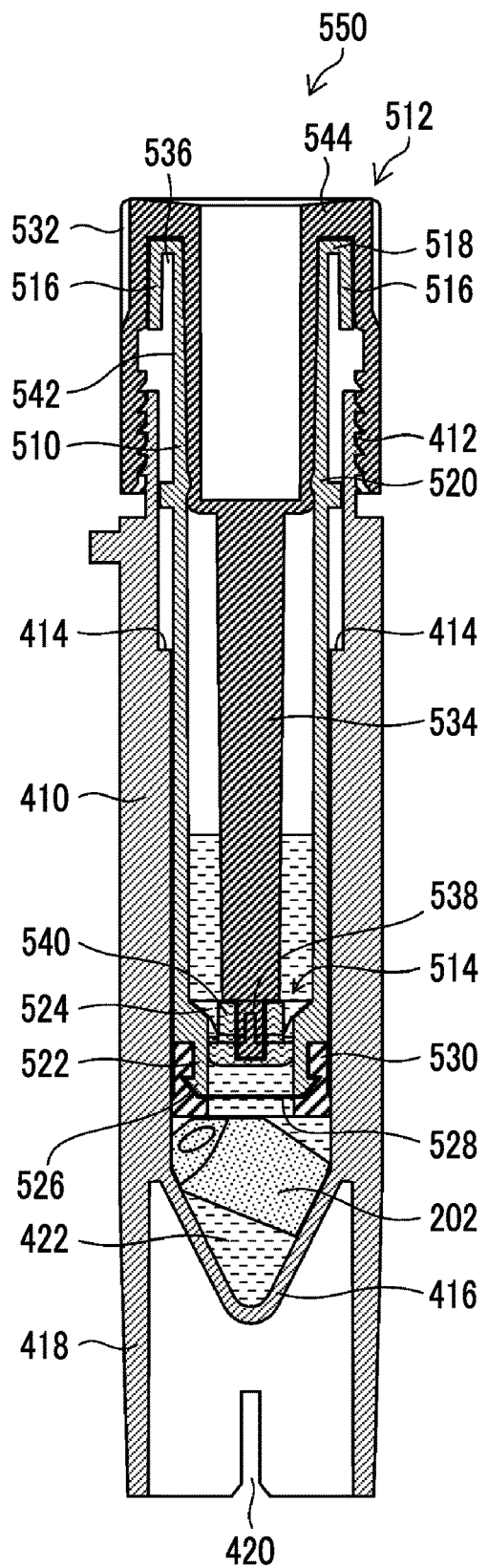
FIG. 7 is a view showing an example of a holding tool for holding a separation instrument.

Next, as shown in FIG. 7, a handle portion 532 is screwed into a screw portion 412. Initially, the handle portion 532 and the cylinder 510 rotate. In a case where the engaging portion 414 of the blood collection container 410 is engaged with a stopper portion (not shown) formed on an outer peripheral surface of the cylinder 510, the rotation of the cylinder 510 is restrained, and the thin-walled portion 518 is broken by twisting. As a result, the cylinder 510 is separated into a main body portion 520 and a diameter expanding portion 516. Furthermore, in a case where the handle portion 532 is rotated, an upper end portion 542 of the main body portion 520 enters a space 536 inside the diameter expanding portion 516. Because the cylinder 510 is pressed downward by an inner surface of a top portion 544 of the handle portion 532, the cylinder 510 further descends.

As the cylinder 510 descends, a filtration membrane 528 held by the cylinder 510 moves toward the side of the bottom portion 416 of the blood collection container 410. In this case, the plasma moves through the filtration membrane 528 to the side of the cylinder 510, and the blood cells cannot pass through the filtration membrane 528 and remain on the side of the blood collection container 410.

Because an outer diameter of a cover 530 is larger than an outer diameter of the main body portion 520 of the cylinder 510, the cylinder 510 descends in a state of being close contact with the inner surface of the blood collection container 410. Accordingly, in the process of fitting the cylinder 510 into the blood collection container 410, there is no possibility that the dilute solution 422 in the blood collection container 410 leaks to the outside through a gap between the blood collection container 410 and the cylinder 510.

In a case where the handle portion 532 is screwed to the screw portion 412 to the lowermost part, the sealing member 514 is fitted into the diameter reducing portion 522. A flow path between the blood collection container 410 and the cylinder 510 is hermetically sealed by the sealing member 514. The sealing member 514 prevents mixing of plasma and blood cells due to back flow.

As described above, the liquid specimen collection tube 550 containing the plasma component separated from the blood is put into the packaging container 10, the opening portion of the packaging container 10 is hermetically sealed to be mailed to a medical institution or a test institution. The liquid specimen collection tube 550 corresponds to a combination of the accommodation instrument 400, the cylinder 510, and the cap 512.

The blood test kit is capable of realizing a method that can analyze an analysis target component with high measurement accuracy even in a case where an amount of blood collected is 100 μL or less. The blood test kit is preferably a blood test kit including a manual which describes information showing accurate measurement is possible even with a small amount of blood collected, such as 100 μL or less, or showing how much blood specimen should be collected by the fiber rod 202 of the blood collection instrument 200.

FIGS. 5 to 7 explain an aspect in which the cylinder 510 and the cap 512 are combined, and then fitted into the accommodation instrument 400, but the present invention is not limited thereto. The liquid specimen collection tube 550 may be configured by separately combining the cylinder 510 and the cap 512. First, the cylinder 510 is fitted into the accommodation instrument 400 containing a blood specimen, and the cylinder 510 is pushed downward the accommodation instrument 400, and therefore the cylinder 510 descends in the accommodation instrument 400. In this case, the plasma passes through the filtration membrane 528 and moves to the side of the cylinder 510. After a sufficient amount of plasma component is moved from the blood specimen into the cylinder 510, the cap 512 is screwed with the accommodation instrument 400, whereby the accommodation instrument 400 and the cylinder 510 are sealed tightly. In addition, a flow path between the blood collection container 410 and the cylinder 510 is sealed tightly by the sealing member 514 provided on the cap 512. The liquid specimen collection tube 550 may be constituted in this manner.

Figure 8:
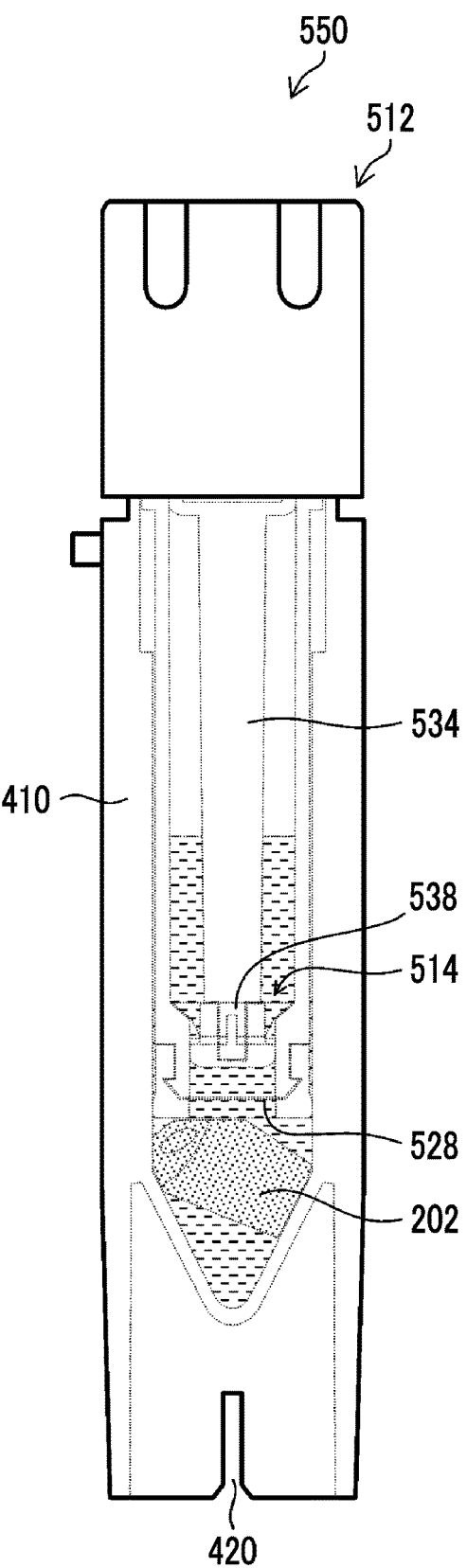
FIG. 8 is an external view of a liquid specimen collection tube shown in FIG. 7.

FIG. 8 is an external view of a liquid specimen collection tube 550 shown in FIG. 7. Hereinafter, a packaging container into which this liquid specimen collection tube is packaged will be described.

Packaging Container

Next, the packaging container 10 into which the liquid specimen collection tube 550, in which blood has been collected using the above-mentioned blood test kit 600, is packaged will be explained. Blood is taken as an example of a liquid to be collected. However, in the present invention, examples of specimens are not limited to blood and include, for example, urine, runny nose, saliva, feces, and the like, which can be used in a test performed with a specimen collected by himself or herself. In addition, as the liquid specimen collection tube 550, a tube in which the cylinder 510 is inserted into the accommodation instrument 400, and the accommodation instrument 400 is hermetically sealed with the cap 512 serves as a liquid specimen collection tube, but the present invention is not limited thereto. For example, a specimen may be put into the accommodation instrument 400, and the accommodation instrument 400 sealed with a cap may be packaged as a liquid specimen collection tube so as to be tested.

Figure 9:
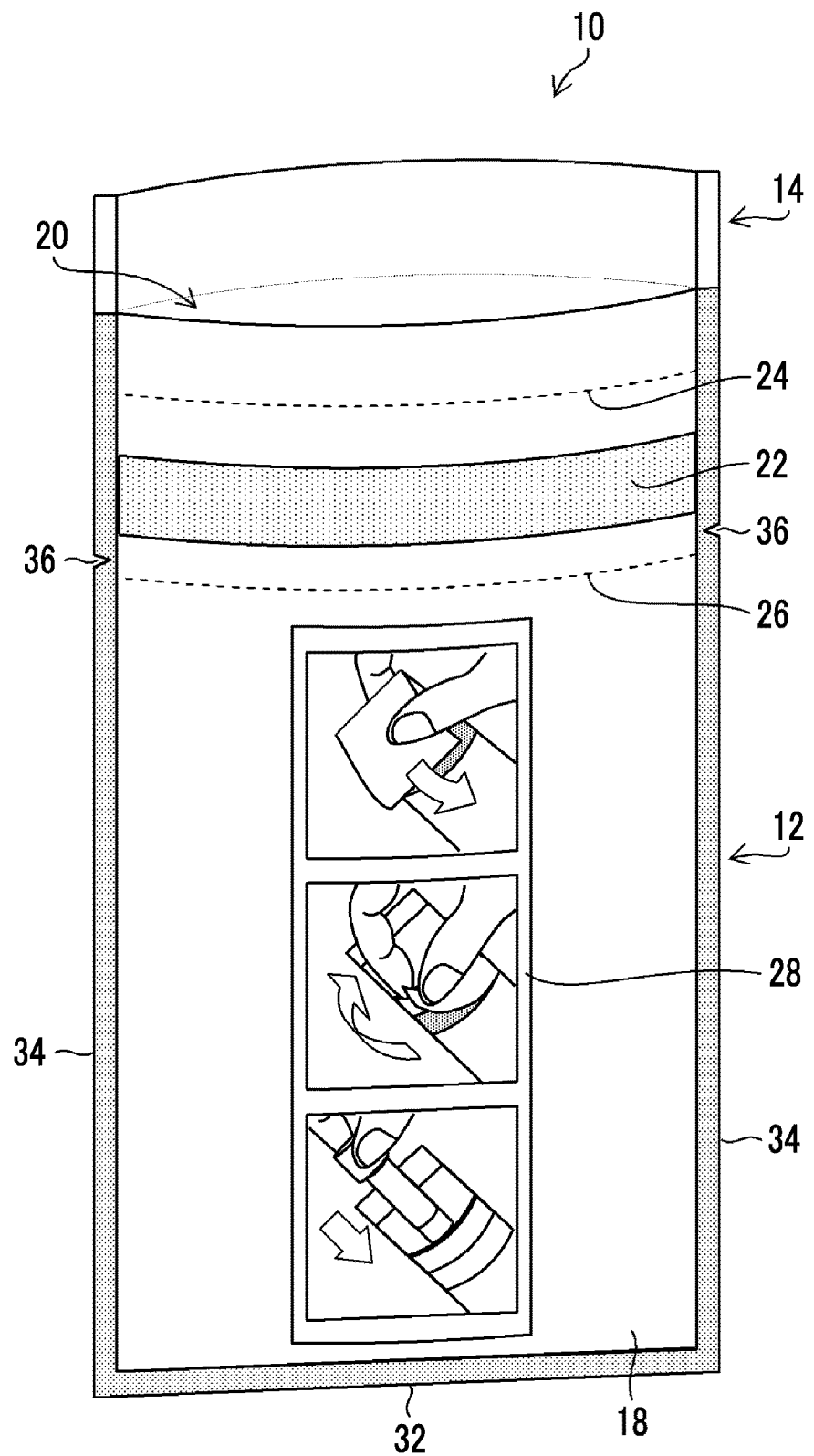
FIG. 9 is a perspective view of a packaging container.
Figure 10:
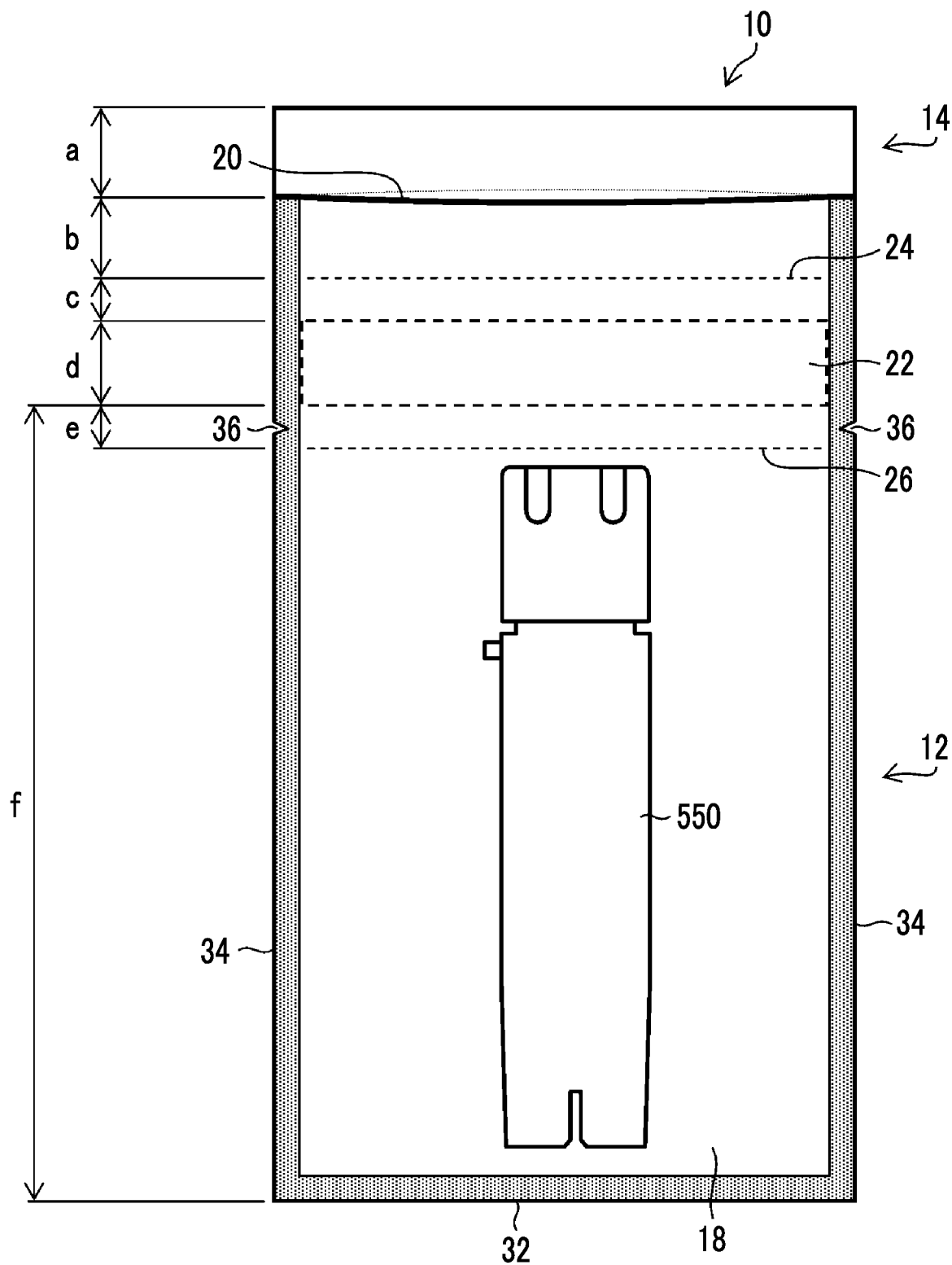
FIG. 10 is a plan view of the packaging container as viewed from a second surface.
Figure 11:
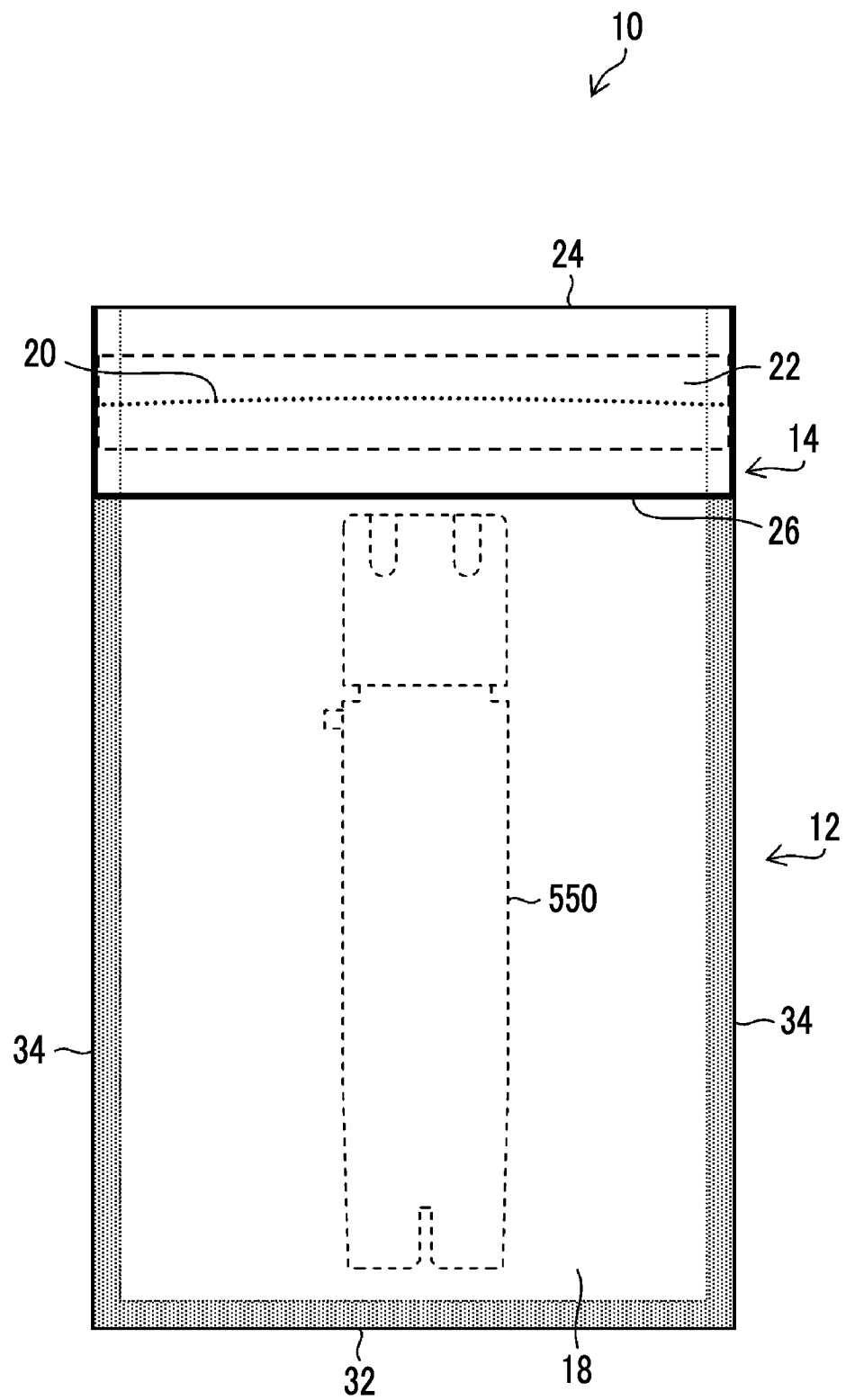
FIG. 11 is a view in which a bag main body portion is folded back at a folded-back portion in FIG. 10.

FIG. 9 is a perspective view of a packaging container. FIG. 10 is a plan view of the packaging container as viewed from a second surface. FIG. 11 is a view in which a bag main body portion is folded back at a folded-back portion in FIG. 10.

As shown in FIGS. 9 and 10, the packaging container 10 is composed of a bag main body portion 12 and a tongue piece portion 14. The bag main body portion 12 is a packaging bag comprising a first surface (denoted by a reference "16" in FIG. 13) and a second surface 18 which define an inner space for housing the liquid specimen collection tube 550, and having an opening portion 20 on one end thereof. End portions other than the opening portion 20 of the bag main body portion 12 are closely attached by, for example, heat sealing or the like. In addition, the tongue piece portion 14 is formed to be continuously extended from the opening portion 20 side of the first surface 16.

The bag main body portion 12 and the tongue piece portion 14 includes an aluminum vapor-deposited layer on an outside thereof. The aluminum vapor-deposited layer can be formed by a general method, and is obtained by, for example, using a winding-type vacuum evaporator, vapor-depositing aluminum in an evaporation source heated to around 1400° C. on a web-like substrate in a vacuum drum maintained at a degree of vacuum of about $10^{-2}$ Pa. Evaporation of moisture from the inside of the packaging container 10 and intrusion of moisture from the outside of the packaging container 10 can be prevented by providing the aluminum vapor-deposited layer on the outside of the bag main body portion 12 and the tongue piece portion 14.

As a material constituting the packaging container, a multilayer film having the aluminum vapor-deposited layer can be used. As a film other than the aluminum vapor-deposited layer, a polyethylene (PE) film and a polyethylene terephthalate (PET) film can be used.

In addition, as shown in FIG. 10, on the second surface 18, an adhesion portion 22 for pasting the folded back second surface 18 and the tongue piece portion 14 is provided so as to be spaced from the opening portion 20. The adhesion portion 22 is formed by applying a gluing agent. As the gluing agent, a general gluing agent can be used. For example, it is possible to use a gluing agent containing an acrylic resin, a styrene resin, a silicone resin, or the like as a base polymer. In general, a peelable seal is attached to the adhesion portion 22, and by peeling this seal at the time of use, the second surface 18 and the tongue piece portion 14 can be pasted to the adhesion portion 22.

In addition, on the second surface 18, a folded-back portion 24 is provided between the opening portion 20 and the adhesion portion 22. The folded-back portion 24 is a position determined by a test subject folding back the bag main body portion 12. A mark such as a line may be present or not present on the second surface 18 as the folded-back portion 24. As a mark, a line such as a straight line or a dotted line may be described, or a crease may be attached. By attaching a crease, a test subject reliably folds back the bag main body portion 12 at the folded-back portion 24, and therefore it is possible to reliably seal the packaging container 10.

A length in a longitudinal direction of each portion of the packaging container 10 satisfies the following relational expression. In a case where a length of the tongue piece portion 14 (a length from the opening portion 20 to a distal end of the tongue piece portion 14) is a, a length from the opening portion 20 to the folded-back portion 24 is b, and a length from the folded-back portion 24 to the adhesion portion 22 is c, the following relational expression is satisfied.

$$a < b + c \qquad (1)$$

By satisfying the above expression (1), in a case of folding back the bag main body portion 12 only at the tongue piece portion 14 (for example, the position of the opening portion 20), because the tongue piece portion 14 does not reach the adhesion portion 22, a test subject again folds back the bag main body portion 12 such that the first surface 16 and the second surface 18 overlap each other. In this manner, it is possible to improve sealability of the packaging container 10 by preventing folding back the bag main body portion 12 only at the tongue piece portion 14, and by folding back the packaging container such that the first surface 16 and the second surface 18 overlap each other.

In addition, in a case where a width of the adhesion portion 22 (a width in an opening direction of the packaging container) is d, the following relational expression is preferably satisfied.

$$c < b < c + d \qquad (2)$$

$$a + b > c + d \qquad (3)$$

By satisfying Expression (2), as shown in FIG. 11, in a case where the tongue piece portion 14 is folded back at the folded-back portion 24, the opening portion 20 can be at the position of the adhesion portion 22. Therefore, the opening portion 20 can be reliably sealed. In addition, by satisfying Expression (3), in a case where the tongue piece portion 14 is folded back at the folded-back portion 24, a distal end of the tongue piece portion 14 can be disposed beyond the adhesion portion 22. Accordingly, in a case of taking out a liquid specimen collection tube from the packaging container 10, it is possible to easily take out the liquid specimen collection tube by peeling off the adhesion portion 22 while holding the distal end of the tongue piece portion 14.

In addition, by satisfying Relational Expression (4), in a case where the tongue piece portion 14 is folded back at the folded-back portion 24, the opening portion 20 can be disposed on a central portion of a width of the adhesion portion 22. Therefore, even in a case where folding back is performed at a position slightly displaced from the folded-back portion 24, the opening portion 20 can be disposed on the adhesion portion 22.

$$2(b-c) \neq d \qquad (4)$$

As specific numerical values of lengths a, b, c, and d, for example, a=20 mm, b=16 mm, c=8 mm, and d=16 mm can be set.

In addition, it is preferable that, an arrival position 26 indicative of a position that is to be the distal end of the tongue piece portion 14 be indicated on the second surface 18 in a case where the bag main body portion 12 is folded back. In this case, positions of the opening portion 20 and the adhesion portion 22 are preferably designed so that the opening portion 20 is disposed on the adhesion portion 22 in a case where the distal end of the tongue piece portion 14 is folded back to be adjusted to the arrival position 26. By indicating the arrival position 26 on the second surface 18, it is possible to reliably seal the opening portion 20 with the adhesion portion 22.

Figure 12:
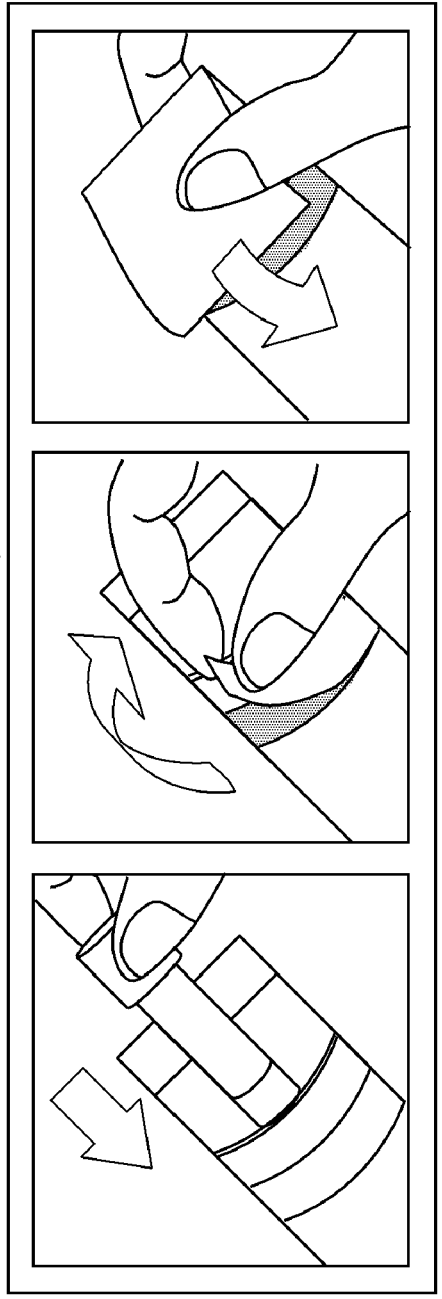
FIG. 12 is a view showing an example of a procedure diagram of operation procedures indicated on the bag main body portion.

It is preferable that a procedure diagram 28 indicative of operation procedures for tightly sealing the packaging container 10 is indicated on the bag main body portion 12. FIG. 12 is a view showing an example of a procedure diagram 28 in which operation procedures are described. The procedure table is described on the second surface 18 in FIG. 9, but may be described on the first surface 16. The procedure diagram 28 may be directly described on the bag main body portion 12, or may be pasted with a seal or the like.

The procedure diagrams shown in FIG. 12 show a diagram (1) in which the liquid specimen collection tube 550 is inserted into the packaging container 10, a diagram (2) in which a seal pasted to the adhesion portion 22 is peeled off, and a diagram (3) in which the bag main body portion 12 is folded back, and the opening portion 20 (the folded back second surface 18 and tongue piece portion 14) and the adhesion portion 22 are pasted, in this order from the left side in FIG. 12. By describing the operation procedure diagram 28 on the bag main body portion 12, it is possible to call attention of packaging procedures of the packaging container 10 also to a test subject who does not read an instruction manual.

In addition, in a case where the liquid specimen collection tube 550 is inserted into the packaging container 10, it is preferable that the adhesion portion 22 is disposed at a position not overlapping with the inserted liquid specimen collection tube 550. That is, as shown in FIG. 10, in a case where, on the second surface 18, a length from the end portion 32 on a side opposite to the opening portion 20 to the adhesion portion 22 is f, the length f of the liquid specimen collection tube 550 is preferably longer than a length in the longitudinal direction. With such a configuration, in a case where the bag main body portion 12 and the tongue piece portion 14 are pasted to the adhesion portion 22, the adhesion portion 22 can be pasted in a plane state, and therefore adhesiveness can be improved. In the present specification, a case where the phrases "on the first surface" and "on the second surface" refers to a case of being on the surface on the outer side of the packaging container 10.

In addition, in the packaging container 10, a notch portion 36 is preferably formed on at least one side portion 34 of the bag main body portion 12, and at a position on a side opposite to the opening portion 20 with the adhesion portion 22 interposed therebetween, in the longitudinal direction of the packaging container 10. The notch portion 36 is provided to assist opening of the packaging container 10. Examples thereof include a triangular notch as shown in FIG. 10, a linear notch, and the like. By providing the notch portion 36, it is possible to easily open the packaging container 10 from the notch portion 36. Therefore, it is possible to easily take out the liquid specimen collection tube 550 from the packaging container 10. As the notch portion 36, it is sufficient as long as the packaging container 10 can be opened in a width direction from the notch portion 36.

Figure 13:
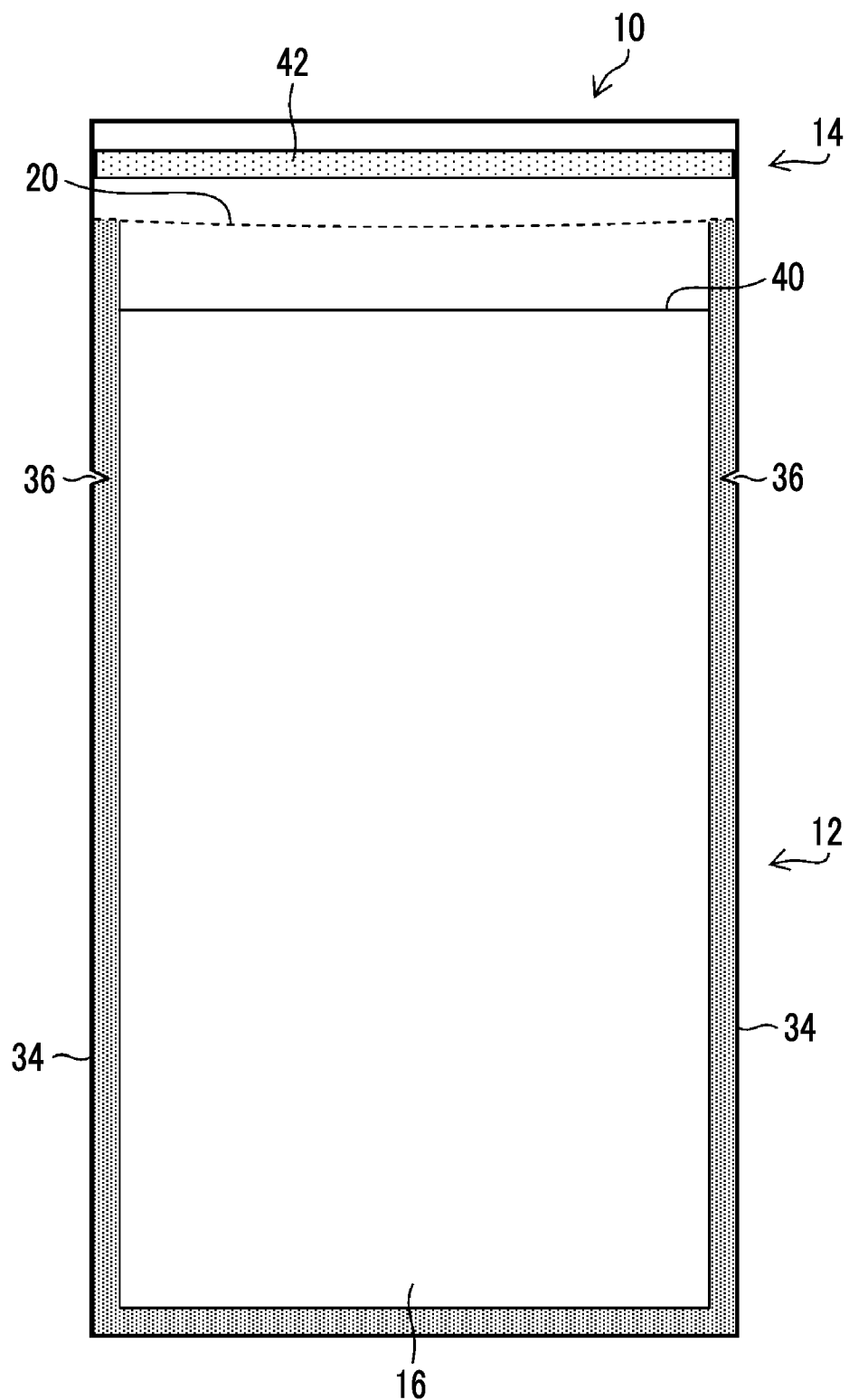
FIG. 13 is a plan view of the packaging container as viewed from a first surface.

FIG. 13 is a plan view of the packaging container as viewed from the first surface in the state of FIG. 10. On the first surface 16, a folded-back position 40 may be provided at a position corresponding to the folded-back portion 24 of the second surface 18. In a case of folding back the bag main body portion 12, it is possible to visually check a folded-back position of the bag main body portion 12 by providing the folded-back position 40 on the first surface 16 in order that the first surface 16 is on the outside. Therefore, it is possible to reliably fold back the bag main body portion 12 at a desired position.

In addition, an adhesion portion 42 to which a gluing agent is applied may be provided on the first surface 16 side of the tongue piece portion 14. By folding back the bag main body portion 12 at the folded-back portion 24, the adhesion portion 42 provided on the first surface 16 of the tongue piece portion 14 comes to the second surface 18 side of the bag main body portion 12. Furthermore, by folding back the bag main body portion 12 to be pasted to the adhesion portion 42, sealability can be improved. As the gluing agent, it is possible to use the same gluing agent as a gluing agent forming the adhesion portion 22 provided on the second surface 18.

Figure 14:
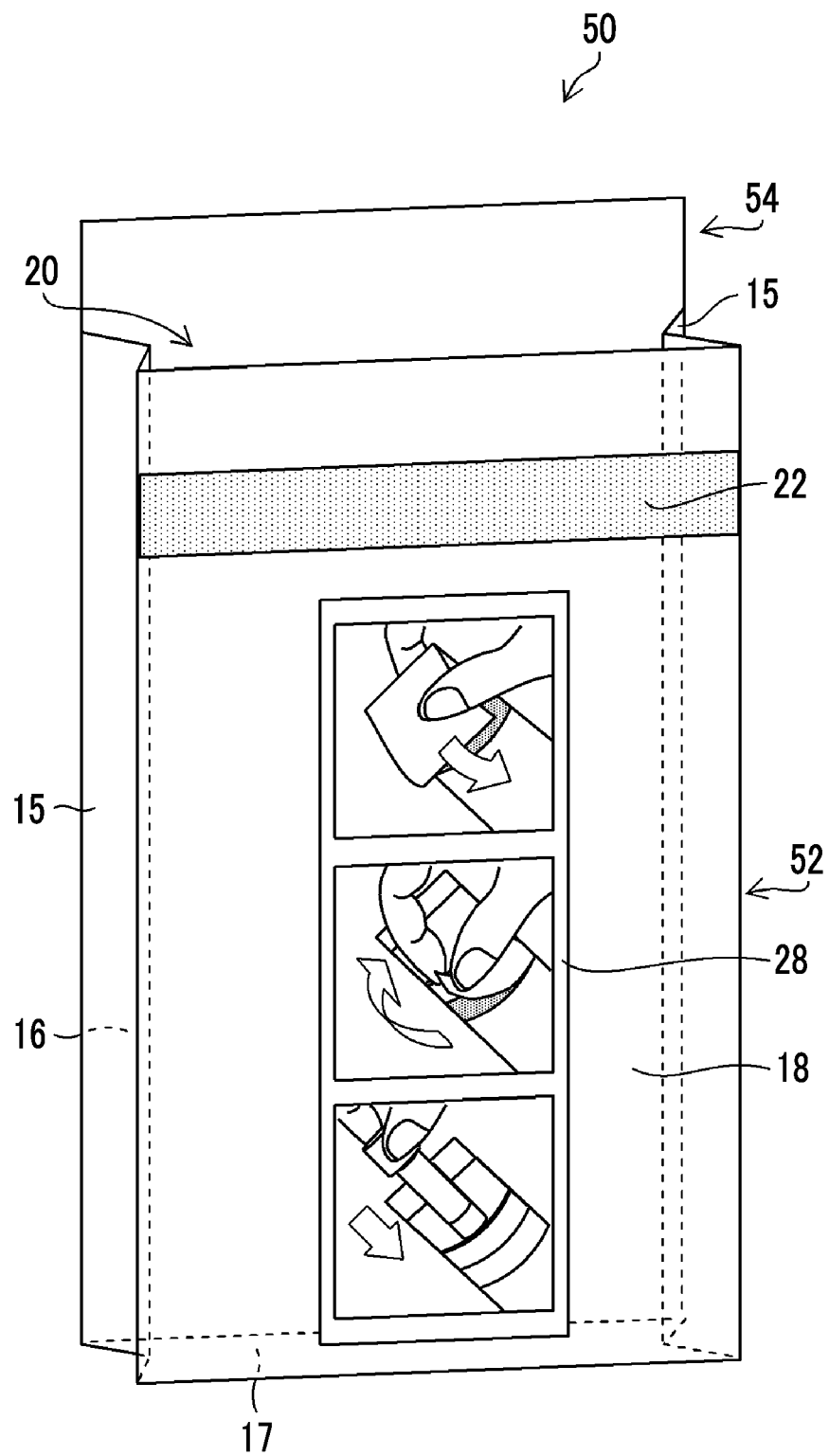
FIG. 14 is a perspective view of a packaging container of another embodiment.

FIG. 14 is a perspective view of a packaging container showing another embodiment. The packaging container 50 shown in FIG. 14 is different from the packaging container 10 of the above-described embodiment in that a bag main body portion 52 is a gusset bag comprising a first surface 16 and a second surface 18, which define an inner space; a pair of gusset portions 15 and 15 provided to be in contact with a side portion of the first surface 16 and the second surface 18; and a bottom surface portion 17. By making the bag main body portion 52 a gusset bag, it is possible to allow the packaging container 50 to have a certain thickness. Therefore, by inserting the liquid specimen collection tube, it is possible to prevent the packaging container 50 from swelling and the adhesion portion 22 from waving. Therefore, it is possible to paste the bag main body portion 52 and the tongue piece portion 54 to the adhesion portion 22 in a plane state.

According to the packaging containers 10 and 50 of the present invention, it is possible to reliably seal the liquid specimen collection tube in the packaging containers 10 and 50. Therefore, errors in tests can be reduced and the accuracy of analysis can be improved. In addition, in a case where it is possible to reliably seal the liquid specimen collection tube in the packaging containers 10 and 50, even in a case where the cap 512 of the liquid specimen collection tube is insufficiently closed, evaporation of a specimen can be prevented, for example.

Blood Analysis Method

A blood analysis method using the blood test kit of the present embodiment will be described. The blood analysis method is preferably carried out by self-blood collection in which a test subject (a patient or a subject) himself or herself uses a lancet to damage the fingertips or the like, and collects blood leaked outside the skin.

A biological sample, which is an analysis target, is blood, and blood is a concept including serum or plasma. Plasma or serum obtained by collecting a small amount of blood by a test subject, diluting with a buffer solution, and separating the blood cells by a filter or through centrifugation, can be preferably used. Components of the blood specimen are preferably a plasma component separated from the blood specimen by separation means. The origin of the blood specimen is not limited to humans, and may be mammals, birds, fish, and the like, which are non-human animals. Examples of non-human animals include horses, cows, pigs, sheep, goats, dogs, cats, mice, bears, pandas, and the like. The origin of a biological sample is preferably human.

As a first aspect of the blood analysis method, a concentration of a target component is analyzed using a standard component constantly present in a blood specimen. The same applies to the standard component constantly present in a blood specimen, as in the explanation described above.

An occupancy rate of plasma components in blood of a test subject is about 55% as a volume ratio, but varies due to changes in salt intake of the test subject. For this reason, in the embodiment, a dilution factor of the plasma is calculated using a standard value of the standard component constantly present in the plasma, thereby analyzing a concentration of a target component in the plasma in the blood specimen using the calculated dilution factor. As a method for calculating a dilution factor, it is possible to obtain a dilution factor by calculating a dilution factor (Y/X) of the plasma component in the blood specimen, from a measurement value (concentration X) of an external standard substance (for example, sodium ion) in a diluted solution of plasma, and a known concentration value (concentration Y: 142 mmol/L in a case of sodium ion) of the above-mentioned external standard substance (for example, sodium ions) contained in the plasma of the blood specimen. Using this dilution factor, a measurement value (concentration Z) of a target component in a dilute solution of the plasma is measured, and by multiplying this measurement value by the dilution factor, it is possible to measure a concentration [Z×(Y/X)] of an analysis target component actually contained in the plasma of the blood specimen.

A concentration of sodium ions and the like can be measured by, for example, a flame photometric method, a glass-electrode method, a titration method, an ion selective electrode method, an enzyme activity method, and the like. In a particularly preferred aspect, sodium ions measurement is carried out by the enzyme activity method utilizing that β-galactosidase is activated by sodium ions, and that a sodium ion concentration and galactosidase activity of a sample diluted with a buffer solution is in a proportional relationship.

In addition, in order to confirm whether the blood test kit in which an amount of a standard component derived from the member is defined is actually used, or whether a method for diluting blood and recovering plasma is normally performed, it is preferable that an additional dilution factor is separately obtained from another standard component in plasma to check whether values thereof match with the dilution factor obtained above. The term "match" means, with respect to two measurement values (a, b), a ratio of their differences to their average values, that is, $|a-b|/\{(a+b)/2\} \times 100$ is 20% or smaller, preferably 10% or smaller, and more preferably 5% or smaller. Accordingly, it is possible to verify that the analysis of a concentration of a target component in a blood specimen is normally performed. Examples of the standard component constantly present in the plasma, which is other than sodium ions and chloride ions are preferably selected from total protein or albumins, and it is more preferable that the component is total protein.

Examples of a method for measuring total protein include the known method such as the biuret method, the ultraviolet absorption method, the Bradford method, the Lowry method, the bicinchoninic acid (BCA) method, and the fluorescence method, and it is possible to select a method to be used appropriately depending on characteristics, sensitivity, specimen amount, and the like of a measurement specimen.

As a second aspect of the blood analysis method, a concentration of a target component is analyzed using a standard component not present in blood. In this case, a blood test kit containing a dilute solution containing a standard component not present in the blood is used.

As a third aspect of the blood analysis method, a concentration of a target component is analyzed using a standard component constantly present in blood and a standard component not present in the blood. By using two standard components in combination, it is possible to perform a more reliable analytical method.

Using sodium ions as a standard component constantly present in blood and using lithium ions as a standard component not present in blood, in a case where sodium ions measurement is carried out by the enzyme activity method (to be described later) utilizing that β-galactosidase activity is in a proportional relationship, and lithium ions measurement is carried out by the chelate colorimetric method (to be described later), a dilution factor of the blood specimen in this case can be calculated by any one of Formulas 1 to 4.

$$X=(A+C)/(B+D) \quad \text{Formula 1}$$

$$X=\{(A^2+C^2)^{1/2}\}/\{(B^2+D^2)^{1/2}\} \quad \text{Formula 2}$$

$$X=a\times(B+D)\pm b \quad \text{Formula 3}$$

(where a and b are coefficients, and data of a dilution factor and (B+D) is acquired in advance to create a standard curve represented in Formula 3.)

$$X=A/B' \quad \text{Formula 4}$$

(where $B'=(A\times D/C)$)

In the above formulas, A, B, C, D, B', and X are defined as follows.

A: Absorbance in a case of coloring a buffer solution
B: Absorbance change after adding plasma
C: Absorbance at a median value of 142 mmol/L of plasma sodium
D: Absorbance at a concentration of sodium ions after diluting plasma
B': Correction value of an absorbance of a standard component not present in the blood of diluted plasma obtained by a dilution factor calculated from an absorbance of plasma sodium
X: Dilution factor of plasma As another calculation method for a case of obtaining a dilution factor, an aspect in which a dilution factor is calculated by Formula 5 using the root-mean-square method, a concentration of an analysis target component in a dilute solution is multiplied by the dilution factor calculated by Formula 5, and therefore a concentration of a target component in the components in a blood specimen is analyzed, is preferable.

Formula 5

$$X=[\{(A/B)^2+(C/D)^2\}/2]^{1/2} \quad (1)$$

A concentration of a target component in the components of the blood specimen can be calculated from a concentration of a target component of the dilute solution based on the above dilution factor.

In addition, by using the packaging containers 10 and 50 of the present invention, it is possible to reduce the influence due to a difference of test subjects due to a manner of closing the cap 512 of the liquid specimen collection tube 550, and therefore a fluctuation due to a manner of closing the cap 512 can be suppressed. Accordingly, by performing correction using the correction parameter, analysis with higher accuracy can be performed.

FIG. 15 is a table showing a closure torque for a cap of a liquid specimen collection tube and an evaporation rate after 7 days depending on whether or not the liquid specimen collection tube is stored in the packaging container. By storing the liquid specimen collection tube in the packaging containers 10 and 50 of the present invention, it is possible to suppress a change in evaporation rate due to the strength of a closure torque.

As described above, in the blood analysis method of the present embodiment, as shown in FIG. 15, a correction table is created in advance based on an evaporation rate of a blood specimen in the packaging container which is in a sealed state; a correction parameter of the blood specimen is set based on the correction table; and a concentration of a target component in the blood specimen on which a test is performed is corrected using the correction parameter. Therefore, analysis can be performed with high accuracy. As shown in FIG. 15, the correction table is preferably created based on a closure torque for a cap of a liquid specimen collection tube, the number of days from a collection date to an analysis date of a blood specimen, and the like, and is preferably created based on at least one thereof. A closure torque for a cap of a liquid specimen collection tube may be obtained by measurement, or may be obtained by the following: gradations are provided on the liquid specimen collection tube and the cap, a relational expression of the gradations and a closure torque is obtained by measurement in advance, and therefore a closure torque is obtained from this relational expression using the gradations.

By using the packaging container of the embodiment of the present invention, an amount of evaporation by storage (mailing) can be suppressed to be low. Accordingly, it is also possible to calculate an amount of components of a blood specimen before evaporation while taking into consideration a numerical value close to an actual amount of evaporation by the correction parameter.

The analysis target component in the analysis method of the present embodiment is not limited, and any substance contained in a biological sample is targeted. Examples thereof include biochemical test items in blood used for clinical diagnosis, markers of various diseases such as tumor markers and hepatitis markers, and the like, and include proteins, sugars, lipids, low molecular weight compounds, and the like. In addition, not only a concentration of a substance is measured, but also an activity of a substance having an activity such as an enzyme is targeted. Measurement of each target component can be carried out by a known method.

In a case of measuring sodium ions, it is possible to use an enzymatic assay by which sodium ions in several μL of a specimen of very low sodium concentration (24 mmol/L or less) diluted with a buffer solution are measured by utilizing that the enzyme activity of the enzyme galactosidase is activated by sodium ions. This method can be applied to a biochemical/automated immunoassay analyzer, and is highly efficient and economical for not required of another measuring instrument for sodium ions measurement.

EXPLANATION OF REFERENCES 10, 50: packaging container
12, 52: bag main body portion
14, 54: tongue piece portion
15: gusset portion
16: first surface
17: bottom surface portion
18: second surface
20: opening portion
22, 42: adhesion portion
24: folded-back portion
26: arrival position
28: procedure diagram
32: end portion
34: side portion
36: notch portion
40: folded-back position
100: lancet
200: blood collection instrument
202: fiber rod
204: space
210: case
212: opening
213: member
214: distal end accommodation portion
216: central portion
218: flange portion
220: base end accommodation portion
222: opening
228: slide groove
240: extrusion rod
242: protrusion
300: locking lever
318: lever
322: operation portion
400: accommodation instrument
410: blood collection container
412: screw portion
414: engaging portion
416: bottom portion
418: leg portion
420: slit groove
422: dilute solution
424: cap
426: packing
500: holding tool
510: cylinder
512: cap
514: sealing member
516: diameter expanding portion
518: thin-walled portion
520: main body portion
522: diameter reducing portion
524: engaging protrusion portion
526: outer flange portion
528: filtration membrane
530: cover
532: handle portion
534: mandrel portion
536: space
538: lower end portion
540: level difference portion
542: upper end portion
544: top portion
550: liquid specimen collection tube
600: blood test kit
602: case

What is claimed is:

1. A packaging container into which a liquid specimen collection tube is configured to be packaged, the packaging container comprising:
a bag main body portion; and
a tongue piece portion,
wherein the bag main body portion is a packaging bag including a first surface and a second surface which define an inner space and having an opening portion provided on one end,
the tongue piece portion is formed to be continuously extended from the opening portion side of the first surface,
the bag main body portion and the tongue piece portion include an aluminum vapor-deposited layer on an outside thereof,
the packaging container further comprises:
an adhesion portion that is provided on the second surface to be spaced from the opening portion; and
a folded-back portion that is provided between the adhesion portion and the opening portion, wherein in a folded state of the bag main body portion, the tongue piece portion is configured to be folded back at the folded-back portion to the opening portion side, and the folded-back portion does not overlap with the adhesion portion,
wherein the folded-back portion is located between the adhesion portion and the tongue piece portion in an unfold state of the bag main body portion, and the adhesion portion overlaps with the tongue piece portion in the folded state of the bag main body portion,
wherein the tongue piece portion has a first length, the opening portion to the folded-back portion has a second length, and the folded-back portion to the adhesion portion has a third length,
wherein the adhesion portion is provided to have a width in an opening direction of the packaging container,
the first length<the second length+the third length,
the third length<the second length<the third length+the width, and
the first length+the second length>the third length+the width;
the opening portion is configured to be placed on the adhesion portion when the tongue piece portion is folded back at the folded-back portion; and
a notch portion is formed on at least one side portion of the bag main body portion, and at a position on a side opposite to the opening portion with the adhesion portion interposed therebetween, in the longitudinal direction of the packaging container.

2. The packaging container according to claim 1, wherein an arrival position indicative of a position of a distal end of the tongue piece portion is indicated on the second surface of the bag main body portion in a case where the bag main body portion is folded back at the folded-back portion.

3. The packaging container according to claim 1,
wherein an operation procedure for sealing the packaging container is indicated on the bag main body portion, and
the operation procedure is a procedure in which the bag main body portion is folded back and the opening portion is pasted to a position of the adhesion portion.

4. The packaging container according to claim 1, wherein the folded-back portion has a crease.

5. The packaging container according to claim 4, wherein a folded-back position is indicated at a position of the first surface, which corresponds to the folded-back portion of the bag main body portion.

6. The packaging container according to claim 1, further comprising an adhesion portion on the first surface side of the tongue piece portion.

7. The packaging container according to claim 1, wherein a length from an end portion on a side opposite to the opening portion on the second surface of the bag main body portion to the adhesion portion is configured to be longer than a length in a longitudinal direction of the liquid specimen collection tube.

8. The packaging container according to claim 1, wherein a notch portion is formed on a side portion of the bag main body portion, and at a position on a side opposite to the opening portion with the adhesion portion interposed therebetween.

9. The packaging container according to claim 1, wherein the packaging bag is a gusset bag.

10. A blood test kit comprising:
a blood collection instrument for collecting a blood specimen;
a dilute solution for diluting the collected blood specimen;
a liquid specimen collection tube including separation means for recovering a plasma component from the diluted blood specimen; and
the packaging container according to claim 1,
wherein a concentration of a target component in the blood specimen is analyzed using a standard component constantly present in blood or a standard component not present in blood but contained in the dilute solution.

11. A blood analysis method which uses the blood test kit according to claim 10, the blood analysis method comprising:
creating a correction table based on an evaporation rate of the blood specimen in the packaging container which is in a sealed state;
setting a correction parameter of the blood specimen based on the correction table; and
correcting a concentration of a target component in the blood specimen using the correction parameter.

12. The blood analysis method according to claim 11, wherein the correction table is created based further on at least one of a number of days from a collection date to an analysis date of the blood specimen, or a closure torque for a cap of the liquid specimen collection tube.

* * * * *